United States Patent [19]
Warters

[11] Patent Number: 6,155,252
[45] Date of Patent: *Dec. 5, 2000

[54] METHOD AND APPARATUS FOR DIRECTING AIR FLOW WITHIN AN INTUBATED PATIENT

[75] Inventor: Robert Davidson Warters, Houston, Tex.

[73] Assignee: Board of Regents, The University of Texas System, Austin, Tex.

[*] Notice: This patent is subject to a terminal disclaimer.

[21] Appl. No.: 09/097,611

[22] Filed: Jun. 15, 1998

Related U.S. Application Data

[63] Continuation-in-part of application No. 08/616,706, Mar. 15, 1996, Pat. No. 5,765,557, which is a continuation-in-part of application No. 08/406,310, Mar. 17, 1995, Pat. No. 5,605,149.

[51] Int. Cl.$^7$ .................................................. A61M 15/00
[52] U.S. Cl. ............................... 128/200.24; 128/204.18
[58] Field of Search .............................. 128/913, 201.21, 128/205.27, 204.18, 207.14, 207.15, 207.16, 207.13, 200.24; 604/43, 45

[56] References Cited

U.S. PATENT DOCUMENTS

| | | |
|---|---|---|
| 3,754,554 | 8/1973 | Felbarg . |
| 3,788,326 | 1/1974 | Jacobs . |
| 3,815,606 | 6/1974 | Mazal ................................. 128/207.16 |
| 3,844,290 | 10/1974 | Birch et al. . |
| 4,026,296 | 5/1977 | Stoy et al. . |
| 4,233,984 | 11/1980 | Walling .............................. 128/207.14 |
| 4,327,720 | 5/1982 | Bronson et al. . |
| 4,416,273 | 11/1983 | Grimes . |
| 4,538,607 | 9/1985 | Saul . |
| 4,595,005 | 6/1986 | Jinotti . |
| 4,646,733 | 3/1987 | Stroh et al. . |
| 4,688,568 | 8/1987 | Frass et al. ......................... 128/207.15 |
| 4,773,412 | 9/1988 | Blom . |
| 4,840,173 | 6/1989 | Porter, III . |
| 5,029,580 | 7/1991 | Radford et al. ..................... 128/207.14 |
| 5,143,062 | 9/1992 | Peckham . |
| 5,309,906 | 5/1994 | LaBaombard ........................... 128/911 |
| 5,322,062 | 6/1994 | Servas . |
| 5,386,826 | 2/1995 | Inglis et al. . |
| 5,443,064 | 8/1995 | Theis et al. . |
| 5,490,498 | 2/1996 | Faithfull et al. ........................ 128/913 |
| 5,605,149 | 2/1997 | Warters . |
| 5,660,175 | 8/1997 | Dayal ................................. 128/207.14 |
| 5,740,796 | 4/1998 | Skog .................................. 128/204.23 |
| 5,765,557 | 6/1998 | Warters . |
| 5,778,872 | 7/1998 | Fukunaga et al. .................. 128/202.27 |
| 5,823,184 | 10/1998 | Gross ................................. 128/207.14 |

FOREIGN PATENT DOCUMENTS 1516118  10/1989  U.S.S.R. .

OTHER PUBLICATIONS

Hirschl et al., "Initial experience with partial liquid ventilation in adult patients with the acute respiratory distress syndrome," JAMA, 275(5):383–389, 1996.

*Primary Examiner*—Aaron J. Lewis
*Assistant Examiner*—Teena Mitchell
*Attorney, Agent, or Firm*—Fulbright & Jaworski, LLP

[57] ABSTRACT

A novel method and apparatus for directing air flow and for removing internal secretions within an intubated patient is disclosed. In broad respects, the invention disclosed is an air conduit assembly positionable within a patient having an inhalation gas pathway and a separate exhalation gas pathway, so that with each successive burst of exhalation gasses forces secretions progressively out of the patient through the separate exhalation gas pathway. The air conduit may be a variety of air conduits positionable within a patient, including an endotracheal tube and a tracheostomy tube. Also disclosed is a novel apparatus and methods for performing partial liquid ventilation of an intubated patient.

15 Claims, 13 Drawing Sheets

METHOD AND APPARATUS FOR DIRECTING AIR FLOW WITHIN AN INTUBATED PATIENT

This is a continuation-in-part of Ser. No. 08/616,706, filed Mar. 15, 1994 which is now U.S. Pat. No. 5,765,557, which is a continuation-in-part application of Ser. No. 08/406,310, filed Mar. 17, 1995, now issued as U.S. Pat. No. 5,605,149.

BACKGROUND OF THE INVENTION

1. Field of Invention

The present invention relates to ventilation of a hospital patient through an air conduit, such as an endotracheal tube or tracheostomy tube, inserted into the trachea of a patient. More particularly, the present invention relates to a flow system that provides for continuous removal of secretions from within an intubated patient, and for providing improved partial liquid ventilation of a patient.

2. Prior Art

Intubation involves the insertion of a conduit into the trachea of a patient. One of the most commonly used conduits is an endotracheal tube. For intubation, the distal end of the endotracheal tube is extended into the trachea of a patient. The endotracheal tube generally terminates in a patient at a position above the carina and interior to a position between the second and fourth thoracic vertebrae. Gasses may then be introduced into the lungs of the patient through the endotracheal tube.

Purposes for intubation include providing mechanical ventilation of a patient's lungs (e.g., when a disease prevents the patient from normal breathing-induced ventilation), and providing a conduit for anesthetic gasses during a surgical procedure. To prevent the escape of gasses past the endotracheal tube once inside of an intubated patient, an inflatable cuff may be included at the distal end of the endotracheal tube. When inflated, the cuff seals the annular passageway between the endotracheal tube and the tracheal wall. This inflatable cuff may be formed integral with and surrounding the endotracheal tube. There are approximately 17,000 patients in critical care units in the United States on any given day, of which approximately 60% may require intubation. Although intubation is often a life-saving maneuver, intubation unfortunately tends to create serious adverse effects on a patient's ability to clear secretions and particles from their lungs.

In a non-intubated person, inhaled particulate matter is normally cleared from the lungs by a patient's natural mucociliary transport system. The natural mucociliary transport system is composed of cells, which line the tracheobronchial tree and which have cilia (tiny hairs) on their surfaces. The cilia sweep particles up so that coughing can expel the particles from the body. These cells also produce mucous that provide a fluid phase to facilitate transport. Secretions from the tracheobronchial tree are also normally removed through the constant motion of the tiny cilia which line the trachea.

In an intubated patient, however, the endotracheal tube tends to impair the functioning of the natural mucociliary transport system. Initiation of a cough requires glottic closure to generate the intrathoracic pressure required to effectively expel material from the trachea. The presence of the endotracheal tube prevents an intubated patients from closing their glottis. Further, ciliary function and mucociliary transport in the trachea, which may be impaired by infection such as pneumonia or tracheobronchitis, is also impaired by the endotracheal tube, which tends to block the upward movement of secretions. Thus, it is common for intubated patients to have internal secretions pool in the patient's lungs distal to the sealing cuff on an endotracheal tube.

Accumulation of fluids, particulate matter, and internal secretions in the lungs of intubated patients give rise to critical problems and infections in these patients, such as atelectasis and pneumonia. The risk of such infection and other problems generally increase with increased length of time of intubation. It is well-documented that a relatively high mortality rate is associated with prolonged intubation. Removal of pooled secretions from intubated patients is, therefore, an integral part of the care of such patients.

The standard technique for removing internal secretions from an intubated patient is to suction pooled secretions directly from the lungs of the patient. This standard technique, however, has significant disadvantages. For example, direct suctioning requires the periodic efforts of a trained health care professional and often occurs on an intermittent basis of about once every one to two hours, due to labor and time constraints. Secretions within the lungs of an intubated patient, therefore, may accumulate and pool for significant time periods. Further, every time the ventilator system is exposed to allow direct suctioning of pooled secretions from an intubated patient, the risk for contamination and subsequent infection tends to increase. Direct suctioning has been associated with severe complications including hypoxemia, cardiac arrhythmias, decreased oxygen delivery, cardiac arrest, mucosal trauma, and raised intracranial pressure.

Partial liquid ventilation is a methodology that is also of great interest in this field. This concept was initially demonstrated by Clark and Gollan in 1966, who showed that gas exchange is accomplished during spontaneous liquid breathing of perfluorocarbon by mice. Later studies have been performed with perfluorocarbon fluids administered to the trachea of adult patients with acute respiratory distress syndrome until the dependent zone of the lung was filled. It would be of great benefit if a system existed to allow easy and reliable partial liquid ventilation of animals, including humans.

SUMMARY OF THE INVENTION

The present invention addresses the problems discussed above by providing a system that directs air flow within an air conduit, enables a continuous removal of secretions from an intubated patient, reduces or eliminates the need for direct suctioning, and allows for partial liquid ventilation of the patient.

In one general respect, the present invention contemplates an air flow assembly positionable within a patient including an air conduit positionable within a patient having an inspiratory pathway and a separate expiratory pathway; and a conduit coupling assembly coupled to the air conduit including a housing having an upper and a lower port. The conduit coupling assembly may also include a recess disposed within the housing to receive secretions from the separate expiratory pathway, and may include an unidirectional valve disposed within the housing to direct the flow of gasses within the air conduit. In addition, the air conduit may have an internal partition positioned along its length that defines the inspiratory pathway and the separate expiratory pathway. The internal partition may be a flexible partition or a rigid partition.

In further general respects, the present invention contemplates an air flow assembly for directing air flow within a patient, including an air conduit positionable within a patient, an inhalation gas pathway formed within the air conduit, and a separate exhalation gas pathway formed within the air conduit. The air flow assembly may also include a housing having a first air port coupled to said air conduit and a second air port capable of being connected to an external gas source. The housing may also include a secretion retaining reservoir that communicates with the separate exhalation gas pathway to collect secretions forced out of said patient through the separate exhalation gas pathway. The housing may further include an air flow control valve to direct inhalation gasses through the inhalation gas pathway and to block the inhalation gasses from entering the exhalation gas pathway. The air conduit may be an endotracheal tube, a tracheostomy tube, or other air conduit positionable within a patient.

In one more detailed embodiment, a flexible partition is provided within the air conduit and is attached to the interior of the air conduit to form the inhalation gas pathway and the separate exhalation gas. A distal flow control valve may also be attached to the air conduit so that it engages the flexible partition to direct the exhalation gasses into the separate exhalation gas pathway. In particular, the distal flow control valve may be a collapsible valve member that urges the flexible partition toward the opposite interior side of the air conduit. Still further, the flexible partition may be connected to said air conduit along two substantially parallel longitudinal lines extending on opposite sides of the air conduit along its length, and the flexible partition may be constructed to lie substantially along the interior surface of one half of the air conduit in its rest position.

The present invention also contemplates including a housing attached to the air conduit. This housing may have a first air flow port coupled to the air conduit, a second air flow port capable of being connected to an external gas source, and an internal air flow control valve positioned to direct inhalation gasses through the inhalation gas pathway and to direct exhalation gasses through the separate exhalation gas pathway. The flexible partition is then forced in operation to a first side of the air conduit during inhalation and is forced in operation to a second opposite side of the air conduit during exhalation.

In a further embodiment, the present invention contemplates an insertable air flow control assembly for directing air flow within an air conduit within a patient, including a frame support member positionable within an air conduit within a patient; and a partition coupled to the frame support member. The partition defines within the air conduit in operation an inhalation gas pathway and a separate exhalation gas pathway. The frame support member may include two longitudinal support rails, and a plurality of ring members coupled to the support rails. A distal flow control valve may also be attached to said frame support member to direct exhalation gasses into the separate exhalation gas pathway.

In another general aspect, the present invention contemplates an air flow assembly for use with an air conduit positionable within a patient, including a conduit coupling assembly having a housing with an upper and a lower port and a conduit connector coupled to the housing; and an expansible conduit coupled to the conduit connector positionable within an endotracheal tube in a co-axial relation. It is also contemplated that the expansible conduit include a wire or plastic stay to provide longitudinal support.

In a further embodiment, the present invention contemplates the conduit coupling assembly further including a recess disposed within the housing to receive secretions; a unidirectional valve disposed within said housing to direct the flow of gasses; an upper conduit connector coupled to the housing; and a lower conduit connector coupled to said housing. It is also contemplated that the housing include an access port communicating with the recess.

In a still further embodiment, the present invention includes an endotracheal tube coupled to the lower conduit connector such that the expansible conduit is positioned within the endotracheal tube.

In a further aspect, the present invention comprises a combination flow director and trap assembly for use with an air conduit positionable within a patient. The assembly includes a housing with an upper flow connector and a lower flow connector; a fluid trap or collector at its lower end; an expansible tube extending from the housing down through the flow connector; and an annular, valved partition defining an annular chamber within the housing below the partition. The lower flow connector is adapted to be connected to the upper or proximal end of the air conduit so as to form an annular passageway between the air conduit and the expansible tube. The upper flow connector is adapted to receive air or other desired gas from a suitable source. The partition includes a one-way flow valve or other device for enabling flow of gas selectively up through the housing.

In another form, the housing further includes a tube extending down through the upper flow connector and connecting at its lower end with the upper end of the expansible tube so as to enable air or other desired gas to flow from a suitable source to the expansible tube. The upper flow connector may then serve as a vent for the flow of gases passing through the one-way valve.

In a further aspect, the present invention provides a novel method for improving the removal of internal secretions from intubated patients. Inspiratory gasses are directed through the middle of the expansible tube, while expiratory gasses are directed between the walls of the air conduit and the expansible tube. Each successive discharge of expiratory gasses moves internal secretions within the patient further up the sides of the air conduit. Secretions collect in a receptacle at the proximal end of the air conduit. The collected secretions may then be removed from the receptacle through standard suctioning techniques or collected by an absorbent material, without the need for direct suctioning of secretions from within the patient at the distal end of the endotracheal tube. Such an invention is useful as well for procedures using partial liquid ventilation of patients, in that proper gas exchange takes place with the oxygen exchange fluid, while allowing for expiration of exhaled gasses. Moreover, the present invention obviates the need for suctioning of secretions in such procedures.

In a further broad respect, the present invention contemplates a method for removing secretions from lungs of an intubated patient including intubating a patient with an air conduit having an inspiratory pathway and a separate expiratory pathway; circulating a gas down said inspiratory pathway and up said separate expiratory pathway under flow conditions sufficient to move liquid within said patient's lungs during exhalation, if said liquid is present, up said separate expiratory pathway; and separating said liquid from said circulated gas at the upper end of said separate expiratory pathway.

In a more detailed respect, the invention contemplates a method for removing secretions from lungs of an intubated patient, including the steps of intubating a patient with a first conduit; supporting an expansible conduit within the first conduit to define an annular passageway within the first conduit; circulating a gas down the expansible conduit and up the annular passageway under flow conditions sufficient to expand the expansible conduit during inhalation and to move liquid within the patient's lungs during exhalation, if the liquid is present, up the annular passageway; and separating the liquid from said circulated gas at the upper end of the annular passageway. In a further embodiment, the method includes the step of sealing off any annular passageway existing between the first conduit and the patient's trachea.

The present invention also finds use in partial liquid ventilation. This concept was initially demonstrated by Clark and Gollan in 1966, who showed that gas exchange is accomplished during spontaneous liquid breathing of perfluorocarbon by mice. Later studies have been performed with perfluorocarbon fluids administered to the trachea of adult patients with acute respiratory distress syndrome until the dependent zone of the lung was filled.

Thus, for partial liquid ventilation, the present invention contemplates an air flow assembly for directing air flow within a patient to facilitate partial liquid ventilation, comprising an air conduit positionable within a patient, the air conduit having an inspiratory pathway and an expiratory pathway formed within said air conduit. Moreover, such an air flow assembly may further comprise an inspiratory inlet tube coupled to said inspiratory pathway and an expiratory outlet tube coupled to the expiratory pathway. In certain embodiments, the air flow assembly may have an inspiratory inlet tube integrally formed with the inspiratory pathway and the expiratory outlet tube is integrally formed with the expiratory pathway.

In other embodiments, the air flow assembly may have the inspiratory pathway and the expiratory pathway formed by a longitudinal partition positioned to divide the air conduit into separate portions, and the partition may divide the air conduit into substantially equal separate portions, forming the inspiratory pathway and the expiratory pathway. The partition may be flexible, or it may be rigid. The air flow assembly may be a tracheostomy tube. In certain other embodiments, the air flow assembly may be constructed wherein the inspiratory pathway and the expiratory pathway are formed by separate tubes within the air conduit.

The present invention also contemplates methods for performing partial liquid ventilation of a patient. In one embodiment, the method comprises intubating a patient with an air conduit having an inspiratory pathway and a separate expiratory pathway, filling the patient's lungs with an oxygen exchange fluid, directing a gas down said inspiratory pathway under flow conditions sufficient to allow gas exchange with the oxygen exchange fluid, and allowing exchanged gas to exit the patient's lungs through said expiratory pathway. In other embodiments, secretions within the patient's lungs are moved out of the patient's lungs during exhalation through said expiratory pathway. In certain aspects, the invention contemplates an intubating step comprising inserting an air conduit within said patient, and inserting an insertable flow control assembly within said air conduit to define with the air conduit an inspiratory pathway and a separate expiratory pathway. The oxygen exchange fluid is a perfluorocarbon fluid, and the air conduit in certain other embodiments may be a tracheostomy tube.

The present invention also contemplates a method of performing partial liquid ventilation of a patient, comprising intubating a patient with an air flow assembly having a separate inspiratory pathway and a separate expiratory pathway, the air flow assembly comprising an air conduit positionable within a patient, the air conduit having the inspiratory pathway and the expiratory pathway formed within the air conduit by a longitudinal partition positioned to divide the air conduit into separate portions with an inspiratory inlet tube coupled to said inspiratory pathway and an expiratory outlet tube coupled to the expiratory pathway. Next the patient's lungs are filled with an oxygen exchange fluid, and a gas is directed down said inspiratory pathway under flow conditions sufficient to allow gas exchange with the oxygen exchange fluid, allowing exchanged gas to exit the patient's lungs through said expiratory pathway. Utilizing this method, the oxygen exchange fluid may be a perfluorocarbon fluid. Also, the present method contemplates that secretions are removed and cleared through the expiratory pathway.

Advantages and features of the present invention, may be better understood by reference to the following description and appended drawings, which form a part of this specification.

BRIEF DESCRIPTION OF THE DRAWINGS

It is to be noted that the appended drawings illustrate only particular embodiments of the invention and are, therefore, not to be considered limiting of its scope, for the invention may admit to other effective embodiments.

DETAILED DESCRIPTION

The present invention contemplates a method and apparatus for directing air flow within an intubated patient to reduce or eliminate the need for direct suctioning of secretions from within the patient. To allow this capability, the present invention provides an air conduit with separate pathways for inspiratory and expiratory gasses. By so doing, each exhalation by the patient forces secretions within the lungs of the patient up and out of the patient, so that they may be collected and removed without the need for direct suctioning at the distal end of the tube that is within the intubated patient. Because the inhalation gasses pass through a separate pathway, they do not force secretions back down into the patient's lung.

Figure 1:
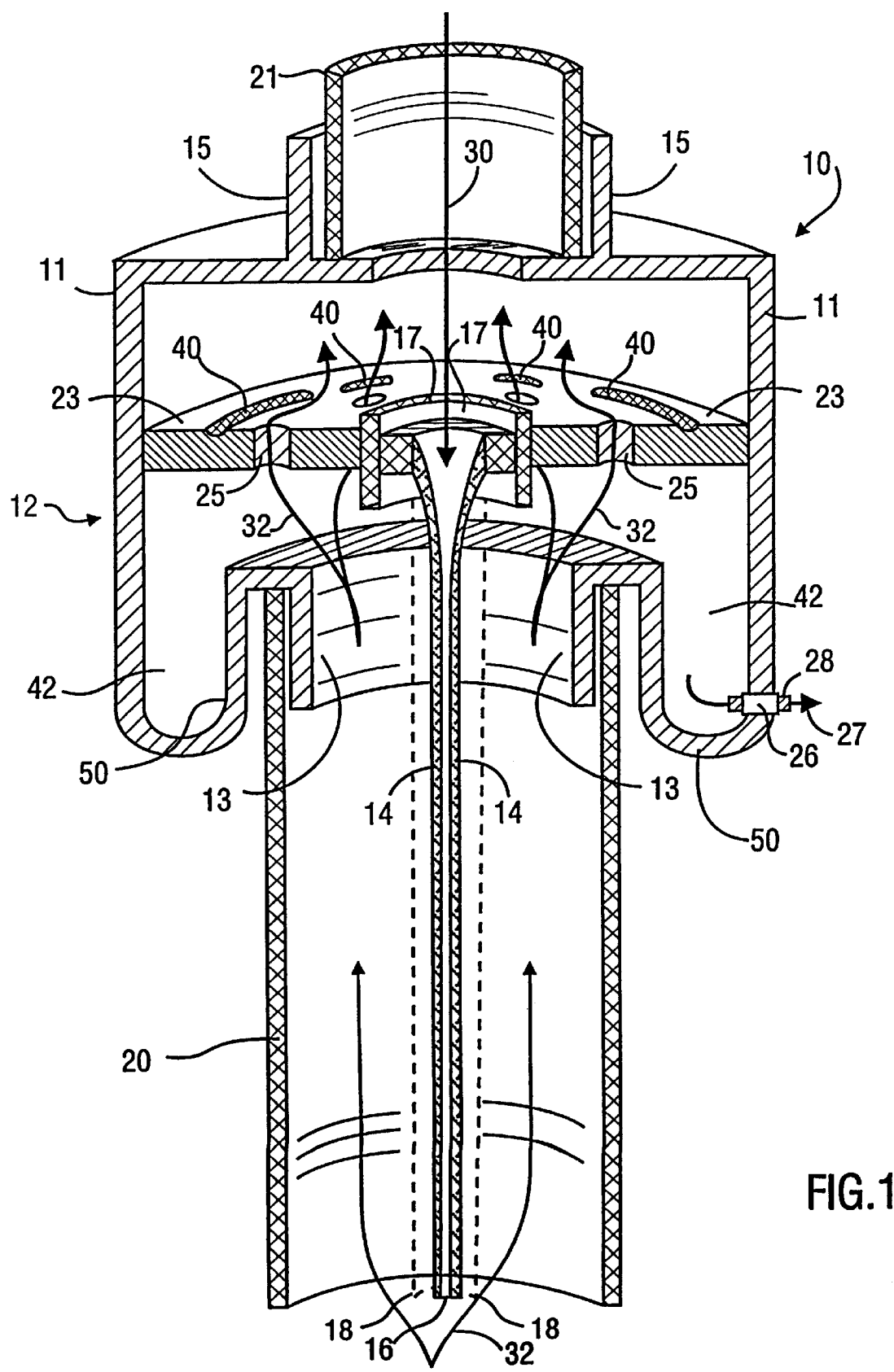
FIG. 1 is diagram of an air flow assembly according to the present invention.

FIG. 1 is one embodiment of an air flow assembly 10 according to the present invention, which includes a conduit coupling assembly 12 and an expansible conduit 14. Expansible conduit 14 may have a natural closed position 16. Expansible conduit 14 may be inflated, for example to expanded position 18, and may be adapted to substantially fill an endotracheal tube. The proximal end of expansible conduit 14 is secured to an internal conduit coupling 17 disposed within conduit coupling assembly 12, such that expansible conduit 14 may be suspended within an air conduit, such as an endotracheal tube 20. Internal conduit connector 17 may be supported within conduit coupling assembly 12 by struts, spokes, or partition 23.

Housing 11 of conduit coupling assembly 12 also includes a lower conduit connector 13 to interface with endotracheal tube 20 and an upper conduit connector 15 to interface with an externally extending conduit, such as may be connected to tubing 21 leading to a source of air, oxygen or other desired gas or mixture of gasses. The lower end of conduit coupling assembly 12 is shaped to define an annular channel or recess 42 capable of serving as a collecting basin or receptacle for liquids and particles expelled from the patient's lungs.

Conduit coupling assembly 12 also includes unidirectional air flow valve 40 disposed above partition 23. Unidirectional air flow valve 40 allows exhalation gasses 32 to pass through port 25 but forces inhalation gasses 30 to travel through expansible conduit 14. It must be noted that a variety of unidirectional valves may be used in the present invention for unidirectional flow valve 40.

Figure 2:
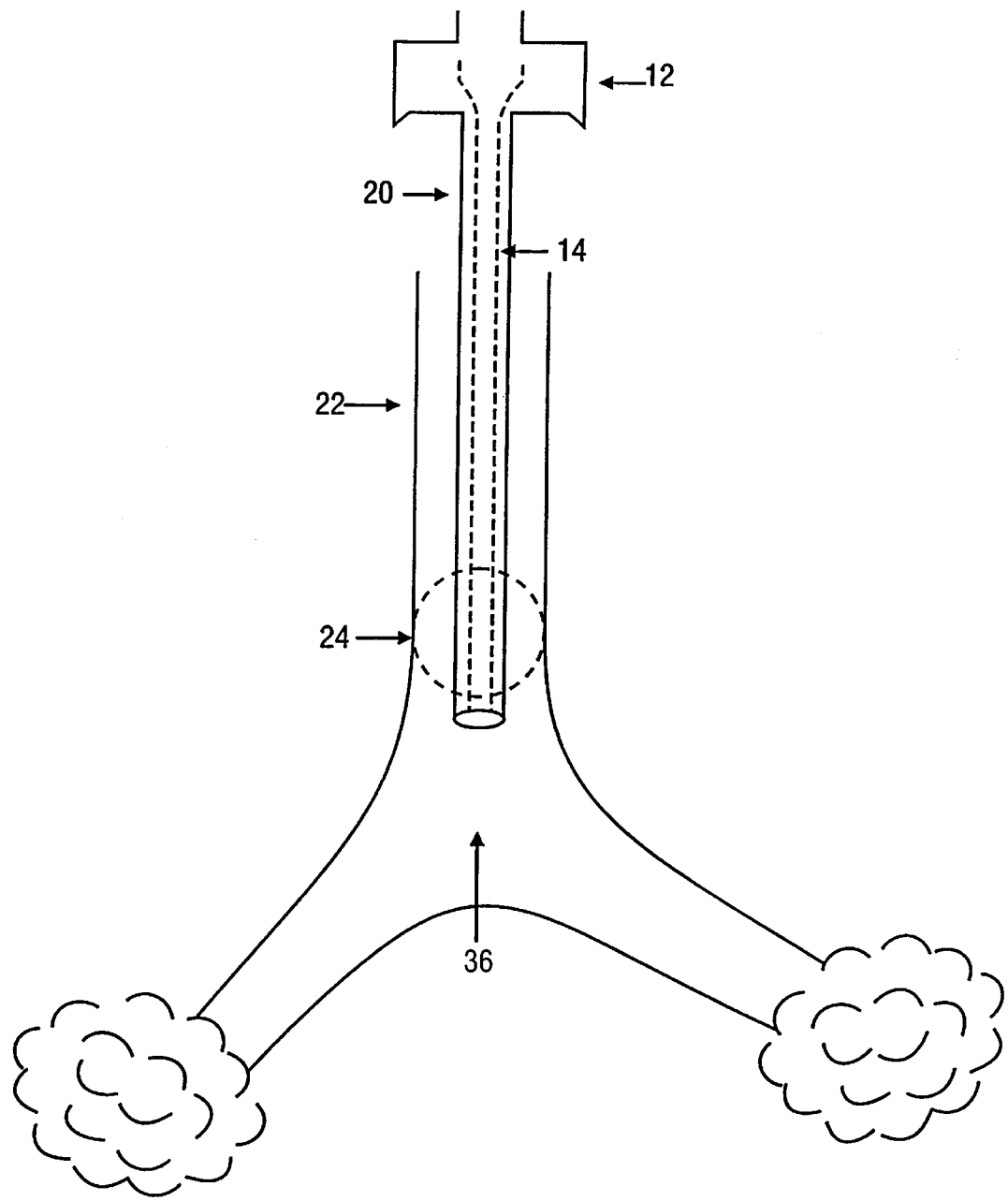
FIG. 2 is a diagram of an air flow assembly within an endotracheal tube located within a patient's trachea.

FIG. 2 is a schematic diagram of endotracheal tube flow assembly 10 according to the present invention coupled to an endotracheal tube 20 positioned within a trachea 22. Endotracheal tube 20 has an inflatable cuff 24. Inflatable cuff 24 may be inflated to seal trachea 22 except for air flow through endotracheal tube 20.

Expansible conduit 14 may be made of any material which will remain closed upon the pressure of exhalation gasses 32, and will expand upon the pressure of inhalation gasses 30. For example, expansible conduit 14 may be a section of flat latex tubing cut to be substantially the same length as endotracheal tube 20 (e.g., 18 inches). The diameter of expansible conduit 14 may be adjusted depending upon the diameter of endotracheal tube 20. Longitudinal stiffness may be given to the expansible conduit 14 by use of a wire or plastic stay. For example, stainless steel wires may be encapsulated by the latex along the longitudinal length of the latex tubing during the dipping process in which the latex tubing is created. In addition, baffles may be attached to the outside of expansible conduit 14 to augment movement of secretions.

Endotracheal tube 20 may be any standard endotracheal tube. For example, endotracheal tube 20 may be a standard endotracheal tube that has a standard endotracheal tube connector at its proximal end and that may be obtained from Sheridan Catheter Corporation or Mallinckrodt Medical, Inc. As contemplated by the present invention, endotracheal tube 20 may also take the form of other air conduits inserted into a patient's trachea or lungs, such as a tracheostomy tube. An endotracheal tube embodiment is described because they are commonly used in intubating patient's.

Conduit coupling assembly 12 may be of a variety of structures, including polyvinylchloride (PVC) fittings that may be purchased from a hardware store. Lower conduit connector 13 is designed to connect to the standard connector at the proximal end of a standard endotracheal tube. Annular channel or recess 42 may be a simple groove within housing 11. Alternatively, wall 50 of recess 42 may be angled to create a v-shaped cross-section that forces secretions toward the outside edge of recess 42. Other configurations for recess 42 may be used so long as recess 42 is capable of holding secretions.

To provide for removal of secretions, housing 11 may also include an access port 26 to which a suctioning device may be connected to suction secretions from recess 42 along path 27. Further, a stopper 28 may be provided to plug port 26 to allow secretions to pool. Alternatively, recess 42 may be filled with an absorbent material that may be removed at periodic intervals. As a further alternative, a permanent suctioning tube or device may be connected to recess 42 in fluid communication with secretions pooling in recess 42.

Figure 3:
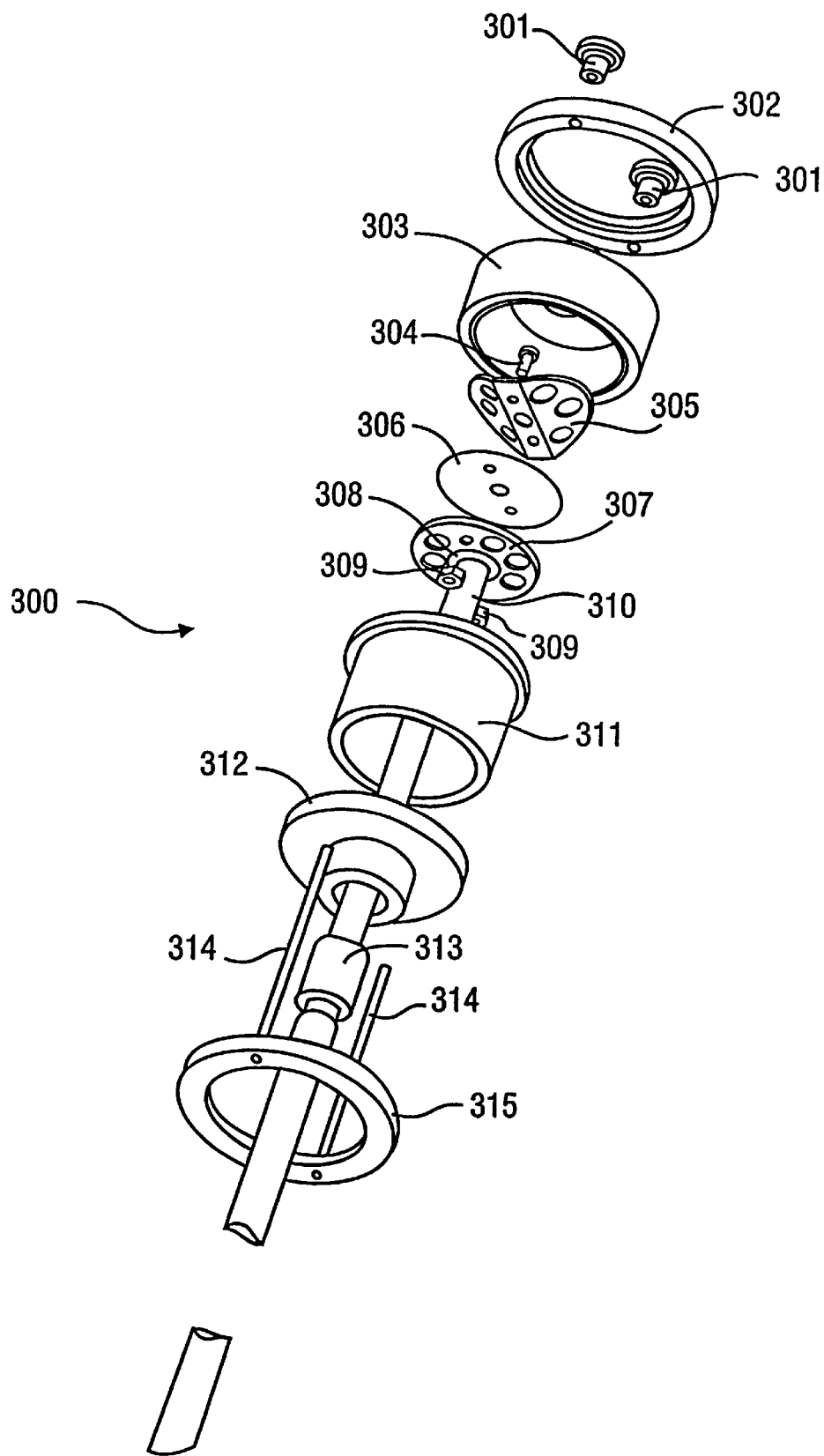
FIG. 3 is a diagram of an alternative embodiment of an air flow assembly according to the present invention.
Figure 4:
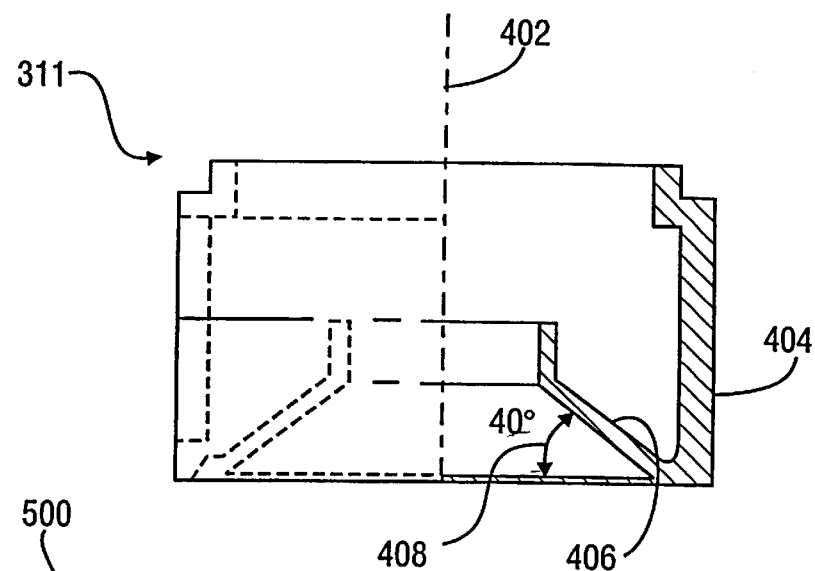
FIG. 4 is a cross-sectional diagram of a v-shaped reservoir for an alternative embodiment of an air flow assembly according to the present invention.

FIG. 3 is a schematic drawing of an alternative embodiment of an endotracheal tube flow assembly according to the present invention. Endotracheal flow assembly 300 includes bottom end ring 315, output cap 312, valve body 311, input cap 303, and top end ring 302. Valve body 311, as shown in FIG. 4, may have a v-shaped recess formed by the intersection of walls 404 and 406. Center line 402 represents the axial center of device 300. The exterior angle 408 formed by walls 404 and 406 may be of various angles, for example, 40° as in the embodiment shown in FIG. 4. Bottom end ring 315 and top end ring 302 have an annular flange in which input cap 303 and output cap 312 rest. Threaded rods 314 are fixed within bottom end ring 315, extend through top end ring 302, and are held by knurled thumb nuts 301. The valve assembly includes primary plate 307, flapper valve 306, and secondary plate 305, which are held together by binding heads 304 and hex nuts 309. Latex tube 310 is coupled to primary plate 307 through O-ring 308. Latex tube 310 extends through endotracheal tube 313 and may include two stainless steel wires embedded along its longitudinal length on opposite sides of latex tube 310.

The parts in endotracheal flow assembly 300 may be made from the following materials:

bottom end ring 315 6061 aluminum threaded rods 314 stainless steel endotracheal tube 313 standard material output cap 312 white Delrin valve body 311 lexan latex tube 310 latex hex nuts 309 stainless steel O-ring 308 rubber primary plate 307 6061 aluminum flapper valve 306 latex secondary plate 305 316 stainless steel binding heads 304 stainless steel input cap 303 lexan top end ring 302 6061 aluminum knurled thumb nuts 301 stainless steel It should be noted that these materials are selected for a particular embodiment. Modifications to the selection of these materials may be made without parting from the present invention.

Looking to FIG. 1, in operation, inhalation gasses 30 are circulated within expansible conduit 14, forcing expansible conduit 14 into an expanded, open position 18. Exhalation gasses 32 are circulated outside of expansible conduit 14 but within endotracheal tube 20. During exhalation, expansible conduit 14 is in natural closed position 16. Unidirectional flow valve 40 acts to force inhalation gasses 30 through expansible conduit 14.

Exhalation gasses 32 flow through unidirectional valve 40 and out through the proximal end of conduit coupling assembly 12. Exhalation gasses 32 force internal secretions within a patient up the interior wall of endotracheal tube 20 and into conduit coupling assembly 12. The secretions collect within annular channel or recess 42. Because inhalation gasses 30 flow within expansible conduit 14, secretions are not forced back down into the patient's lungs. Without endotracheal tube flow assembly 10, which provides separate paths for inhalation gasses 30 and exhalation gasses 32, internal secretions would pool within a patient at the base of the tracheobronchial tree 26.

Experimentation with an endotracheal tube flow assembly, according to the present invention, has shown that secretions tend to be forced up the walls of endotracheal tube 20 by each successive burst of exhalation gasses 32. The present invention, therefore, allows expelled secretions to be collected and removed without having to contaminate the air conduit system within the patient. Further, such collected secretions may be continuously removed, if so desired.

Figure 5A:
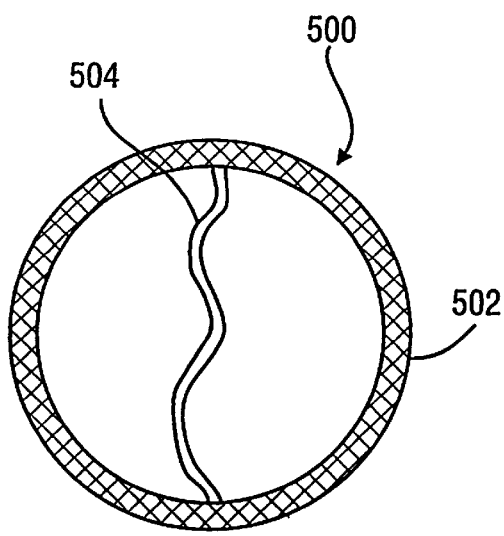
FIG. 5A is a cross-sectional diagram of an alternative embodiment of an air flow assembly according to the present invention having a flexible interior partition.
Figure 5B:
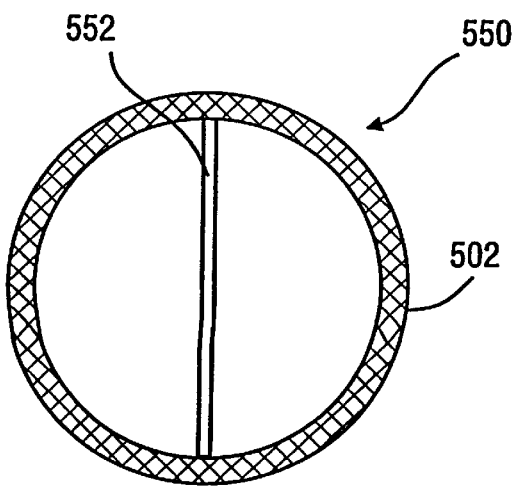
FIG. 5B is a cross-sectional diagram of an alternative embodiment of an air flow assembly according to the present invention having a rigid interior partition.

As mentioned above, the present invention, in broad respects, contemplates directing the air flow within an intubated patient to provide separate pathways for inspiratory and expiratory gasses. Thus, modifications to the above described structures are possible without parting from the present invention. FIG. 5A and FIG. 5B are two examples of such modifications. Alternative embodiment 500 shown in FIG. 5A provides separate inspiratory and expiratory pathways by inserting a flexible partition 504 into endotracheal tube 502. Alternative embodiment 550 shown in FIG. 5B provides separate inspiratory and expiratory pathways by inserting a rigid partition 552 into endotracheal tube 502. Both flexible partition 504 and rigid partition 552 may be made integral with endotracheal tube 502, if desired. In contrast to the embodiments shown in FIGS. 1–4, these embodiments do not rely upon a collapsible tube to provide the separate pathways. The valve and reservoir assemblies described above would be equally applicable to these embodiments as well, although some modifications may be necessary.

FIGS. 6A, 6B, 6C and 6D show a further embodiment of an air flow assembly according to the present invention that uses a flexible partition to create separate inspiratory (or inhalation) and expiratory (or exhalation) pathways. In broad respects, the device shown in FIGS. 6A, 6B, 6C and 6D includes an air conduit with a flexible partition that is attached along a longitudinal extension of the air conduit. In particular, the flexible partition may be attached on opposite sides of the interior wall of the air conduit in a substantially parallel relationship. This flexible partition may be constructed such that it will lay along one-half of the interior wall of the air conduit. As discussed above, the air conduit may be any device that is inserted into a patient's respiratory system to provide air pathways. In particular, the present invention is applicable to tracheostomy tubes and endotracheal tubes.

Figures 6A, 6B:
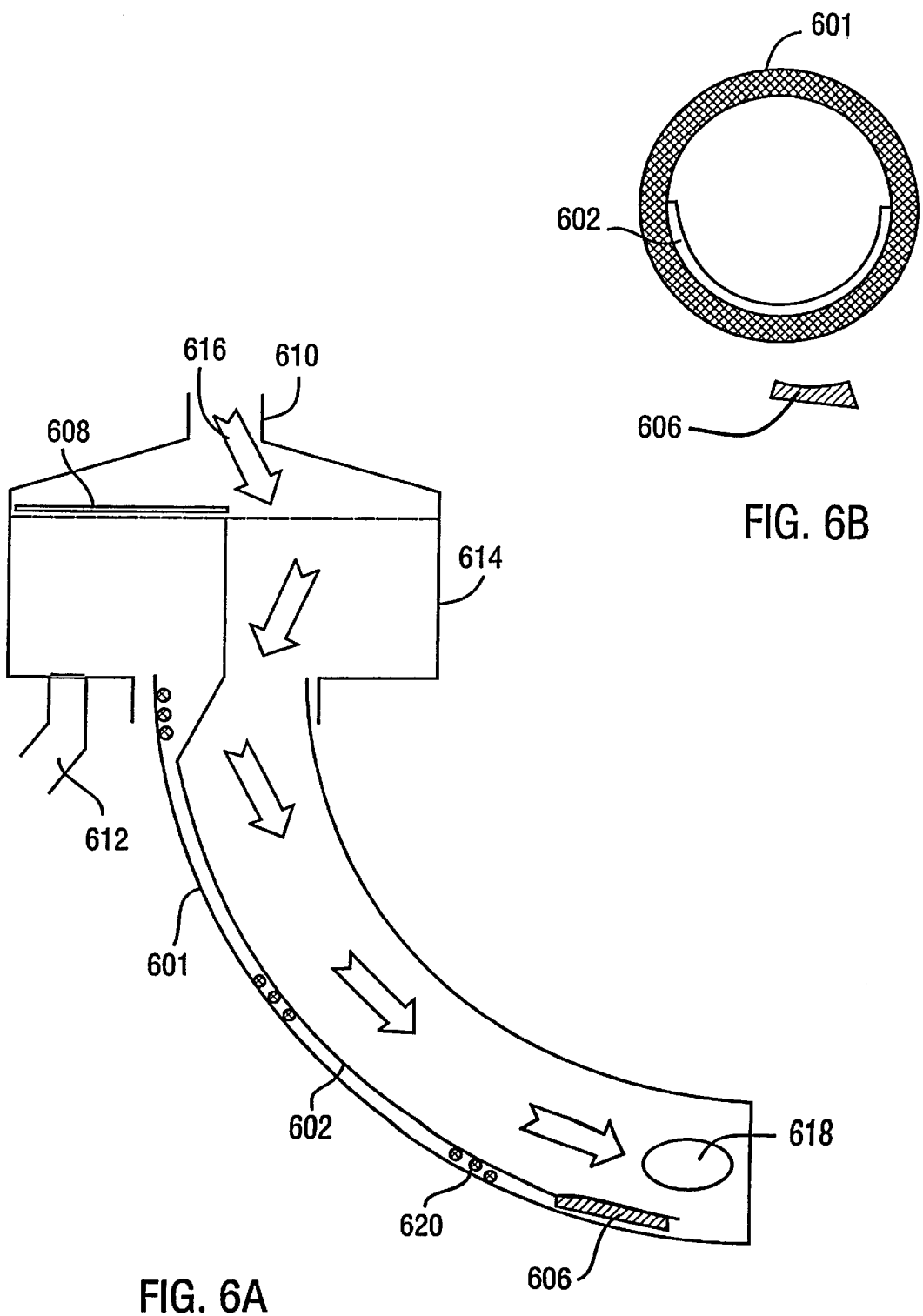
FIG. 6A is a cross-sectional side view of an alternative embodiment of an air flow assembly according to the present invention during the inhalation process.
FIG. 6B is a cross-sectional end view of an alternative embodiment of an air flow assembly according to the present invention during the inhalation process.
Figures 6C, 6D:
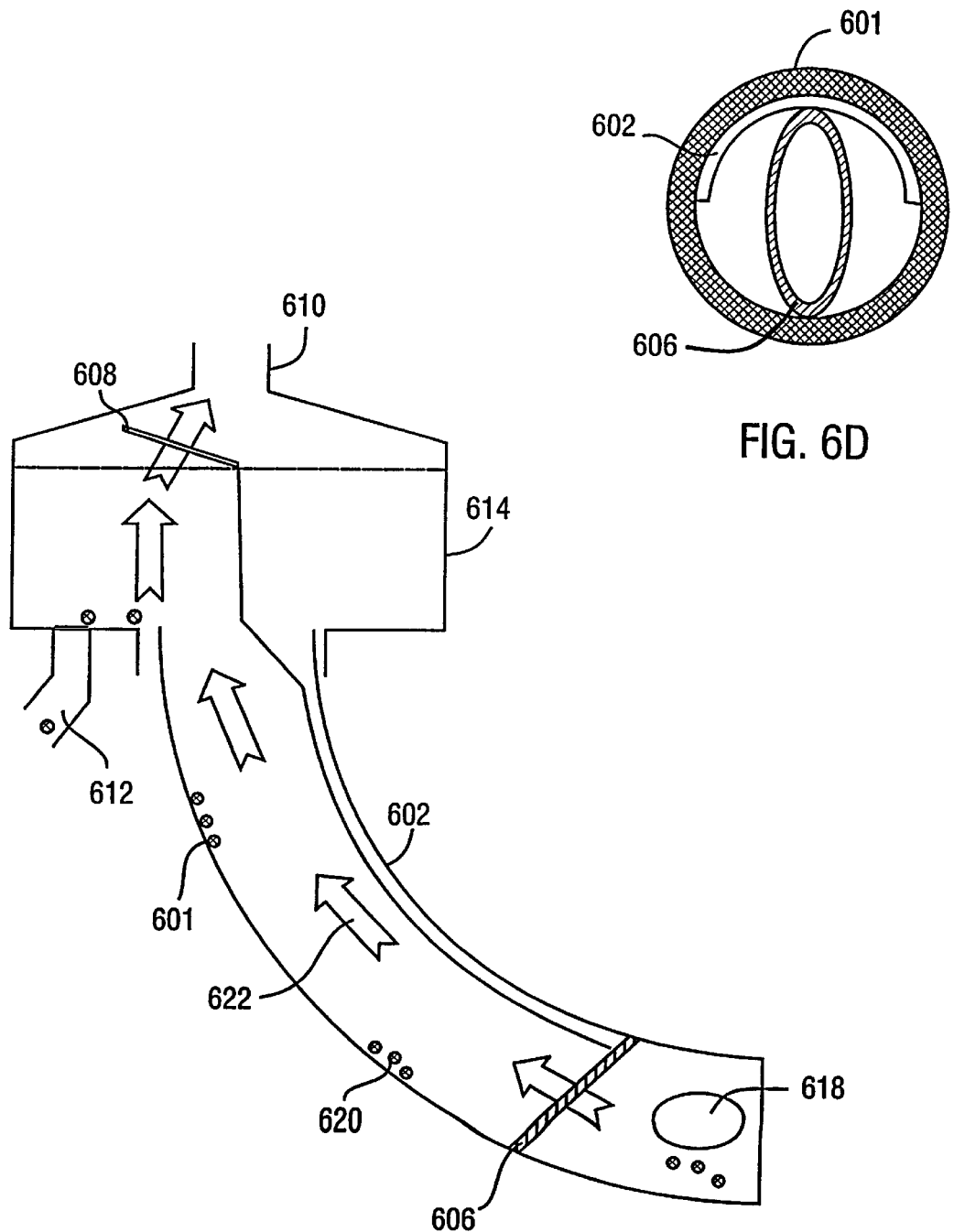
FIG. 6C is a cross-sectional side view of an alternative embodiment of an air flow assembly according to the present invention during the exhalation process.
FIG. 6D is a cross-sectional end view of an alternative embodiment of an air flow assembly according to the present invention during the exhalation process.

In general, FIGS. 6A and 6B show the embodiment during the inhalation process, and FIGS. 6C and 6D show the embodiment during the exhalation process. As shown in FIGS. 6A and 6B, the inhalation pathway is formed between one side of the air conduit and the flexible partition, which has been forced shut against the opposite interior wall. As shown in FIGS. 6C and 6D, the exhalation pathway is formed between the other side of the air conduit and the flexible partition, which has been forced open against the opposite interior wall. A small collapsible valve positioned near the distal end of the flexible partition holds the flexible partition open during exhalation. This may be the rest or natural position of the collapsible valve. The pressure to force exhalation air flow may come from the recoil pressure a patient's lungs. The pressure from inhalation gasses forces the valve and the flexible partition closed against the interior wall of the air conduit as shown in FIGS. 6C and 6D. At the proximal end of the embodiment as shown in FIGS. 6A and 6C, a housing or manifold may be positioned to direct air flow to and from the ventilator (or other suitable gas source) into the air conduit and the air flow assembly. It is noted that the pressure to force the inhalation air flow may come from the patient, as well as an external mechanical source. The housing or manifold may also include a drain to remove secretions that are forced out through the expiratory pathway.

Figure 7A:
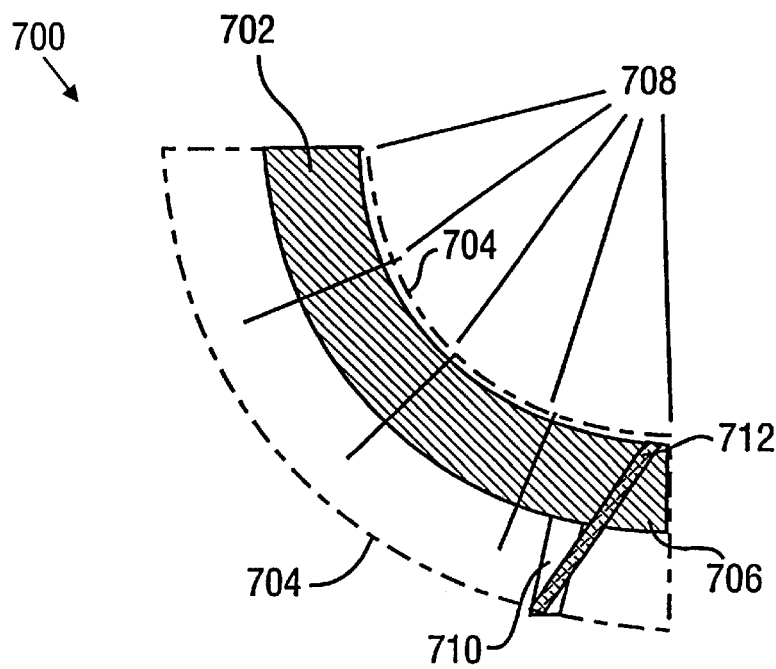
FIG. 7A is a cross-sectional side view of an insertable embodiment of an air flow assembly according to the present invention during the exhalation process.
Figure 7B:
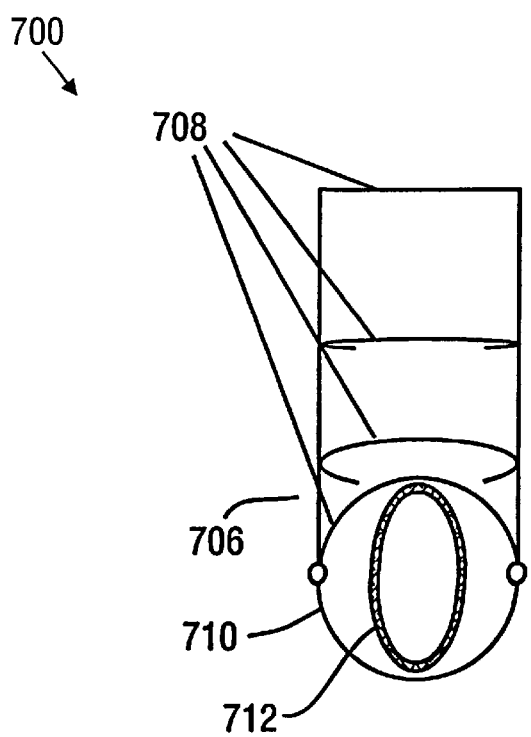
FIG. 7B is a cross-sectional front view of an insertable embodiment of an air flow assembly according to the present invention during the exhalation process.

The present invention further contemplates an insertable air flow assembly that may be positioned within an air conduit as shown in FIGS. 7A and 7B. In broad respects, this insertable embodiment includes a frame that supports the flexible partition and the distal valve. This structure contrasts with the embodiment shown in FIGS. 6A, 6B, 6C and 6D in which the partition is attached to, or integral with, the air conduit. The support frame as shown includes two rails that run the length of the embodiment and multiple rings connected between these two rails. The diameter of the rings may be chosen such that the insertable embodiment fits substantially flush against the interior walls of the air conduit into which it is inserted.

The embodiment shown in FIGS. 6A, 6B, 6C and 6D will now be described in more detail. As mentioned above, FIGS. 6A and 6B depict the state of the air flow assembly during inhalation, and FIGS. 6C and 6D depict the state of the air flow assembly during exhalation.

Looking to FIGS. 6A and 6C, a flexible partition 602 is coupled to an air conduit 601, such as an endotracheal tube or a tracheostomy tube. The arrows (618 and 622) in FIGS. 6A and 6C represent the direction of the gas flow through the embodiment. The flexible partition 602 may be formed integral with the air conduit during construction of the air conduit or may be attached in some other manner, for example with the use of an appropriate glue. At the proximal end of the device, the air conduit 601 is attached to a proximal manifold or housing 614 through which the inhalation gasses 616 and exhalation gasses 622 flow. The proximal manifold or housing 614 may be also be attached to a ventilator through connection port 610. The proximal manifold or housing 614 may also include a check valve 608 for regulating air flow. As seen in FIG. 6A, check valve 608 forces the inhalation gasses 616 to flow through an inhalation pathway formed between the flexible partition 602 and the interior wall of the air conduit 601. As shown in FIG. 6C, the check valve 608 allows exhalation gasses 622 to flow through a separate exhalation pathway formed between the flexible partition and the opposite interior wall of the air conduit 601.

Referring to FIGS. 6A and 6B, it is seen that during inhalation, that the inhalation gasses 616 force the flexible partition 602 against the interior wall of the air conduit 601. This positioning is depicted in more detail in the cross sectional view shown in FIG. 6B. The distal valve 606 may be coupled the interior wall of the air conduit 601 and extend toward flexible partition 602, urging flexible partition 602 against the opposite interior wall of air conduit 601. Distal valve 606 may also be attached to flexible partition 602. In the case of a endotracheal tube, distal valve 602 and flexible partition 602 may be located proximal to a Murphy Eye 618, if such is located on the endotracheal tube. Thus, during operation, the inhalation gasses 616 flow from the air source, such as a ventilator, through the inhalation pathway as shown in FIG. 6B and into the patient's lungs. During inhalation, therefore, the distal valve 606 and the flexible partition 602 may be forced against the interior wall of air conduit 602. Distal valve 606 may be made of a loop of thin stainless steel wire or nylon fishing line. For example, approximately 3 cm segment of nylon fishing line may be used to form a loop. The last 5 mm of each end of the segment may then be positioned together to form a support arm for the loop. This support arm may then be bent to form an angle between the support arm and the loop (e.g., 100° to 110°). The support arm may then be coupled to the air conduit with the loop extending toward the distal end of the air conduit and urging the flexible partition upward 602.

Looking to FIGS. 6C and 6D, it is shown that the exhalation gasses 622 flow out of the patient through a separate air pathway than the air pathway for inhalation gasses 616 shown in FIGS. 6A and 6B. As shown in the cross-sectional view in FIG. 6D, the distal valve 606 is in an open position during exhalation. In the embodiment shown in FIGS. 6A–D, the natural rest position for distal valve 606 is the open position shown in FIGS. 6C and 6D. It is also seen from FIGS. 6C and 6D that the flexible partition 602 is forced by the exhalation gasses 622 toward the opposite side of the air conduit 601. As discussed above, by providing a separate exhalation pathway, secretions 620 are forced out the exhalation pathway through the air conduit 601 into the proximal manifold or housing 614. Proximal manifold or housing 614 may be provided with a retaining area or recess in which the secretions pool 620. Secretions 620 may be removed through drain 612. Also as shown in FIG. 6C, the check valve 608 provides for air flow from the patient's lungs through the air conduit 601 and out of proximal manifold or housing 614. It is also understood that check valve 608 may be a unidirectional valve as discussed previously.

In operation, looking to FIG. 6A, inhalation gasses 616 travel through a first air pathway from outside the patient through the proximal manifold or housing 614, through air conduit 601, and into the patient's lungs. In this inhalation process, the flexible partition 602 is forced to one side of the air conduit, effectively opening up substantially the entire interior volume of the air conduit for the inhalation air flow. Looking to FIG. 6C, the exhalation gasses 622 pass through a separate exhalation pathway from the patient's lungs, through air conduit 601, and ultimately out through the proximal manifold or housing 614. In this exhalation process, the flexible partition 602 is forced to the other side of the air conduit, again effectively opening up substantially the entire interior volume of the air conduit for the exhalation air flow. Secretions 620, however, remain on the exhalation side of flexible partition 602 and are forced out of the patient by each successive burst of exhalation gasses from the patient. It is noted that the pressure to force the exhalation air flow out of the patient may be from the recoil pressure of a patient's lungs. Because of the separate inhalation pathway created by the flexible partition 602, the inhalation gasses 616 do not force secretions 620 back down into the patient's lungs. Furthermore, by using the flexible partition 602 to create the separate air pathways, substantially all of the interior volume of the air conduit may be utilized during inhalation and exhalation. This reduces the air flow resistance experienced within the air flow assembly both during inhalation and during exhalation, which is a desirable result to avoid unnecessary stress on the patient and the air conduit system.

The insertable embodiment 700 shown in FIGS. 7A and 7B will now be described in more detail. The insertable embodiment 700 of an air flow assembly according to the present invention may be constructed to be inserted into any of a variety of air conduits positionable within a patient, such as an endotracheal tube and a tracheostomy tube. The insertable embodiment 700 may include a flexible frame which in turn may include partition rails 706 and a plurality of rail support rings 708 as shown in FIGS. 7A and 7B. The diameter of the rail support rings 708 may be chosen such that the diameter is substantially the same as the diameter of the air conduit 704. Thus, the interior wall of the air conduit 704 is proximal the rail support rings 708. It is noted, however, that a variety of dimensions may be chosen. The support frame may be made by drawing a pattern associated with the chosen shape of the structure on a thin plastic film (e.g., transparency film) or a stainless steel sheet. Once the pattern is cut out for the desired shape, the film or sheet can be folded and glued together to achieve the chosen structure.

The support frame may also include a distal valve support member 710 that is attached to one of the partition rings 708. A distal valve 712 may then be attached to the distal valve support member 710 and may extend toward flexible partition 702, as shown in FIGS. 7A and 7B. Further, the insertable embodiment 700 may be connected to a proximal manifold or housing as shown in FIGS. 6A and 6C.

In operation, the insertable embodiment 700 is first inserted into an air conduit. During inhalation, the distal valve 712 and flexible partition 702 are forced to the interior wall of the air conduit 704, opening up an inhalation pathway for the inhalation gasses. The natural, rest position for distal valve 712 may be the open position for exhalation as shown in FIGS. 7A and 7B. During exhalation, the distal valve 712 remains open and the flexible partition 702 remains against the opposite side of the air conduit to provide a separate exhalation pathway for exhalation gasses.

The proximal manifold or housing 614 and accompanying structures may be constructed in a variety of shapes and arrangements. One embodiment is shown in FIGS. 8A, 8B, 8C and 8D. Looking to FIG. 8A, the housing body 802 may be cylindrical in shape, tapering to an external conduit engaging portion 807. External conduit engaging portion 807 may be connected to an external gas source, such as a ventilator. Housing body 802 may have screw holes 806 formed into its bottom surface 803. As shown in FIG. 8D, a sealing collar 816 may fit on the bottom surface 803 of the housing body 802 and may include access holes 817 through which screws communicate with screw holes 806. The screw or bolt circle 818 is shown in FIG. 8D as a dotted line. The sealing collar 816 may also include an access port 821 through which the air conduit assembly enters the housing body 802.

As discussed above, the housing may include a flow control valve for directing air flow within the housing. The structure of this flow control valve and the internal structure of the housing may be modified depending upon the air conduit and the flow assembly structures chosen to create separate inhalation and exhalation pathways. One such structure that may be used as the air conduit is the soft PVC tubing portion of a commercially available endotracheal tube or tracheostomy tube. This soft PVC tubing may be split in half along its longitudinal length. The separate inhalation and exhalation pathways may then be formed using a vinyl film as a flexible partition. This vinyl film is laid across one half of the split PVC tubing and attached using a layer of vinyl cement applied to the edges of the tube halves. The second half of the PVC tubing may then be glued with vinyl cement to the other half of the PVC tubing and the flexible vinyl film to form again a whole PVC tube. Thus, the vinyl film is effectively glued between the two halves of the tubing to create an air conduit with an internal flexible partition. The excess vinyl film on the outside of the tubing can be trimmed. Silicon gel sealant may be applied to gaps and seams to provide a better seal of the entire construction.

Figure 8A:
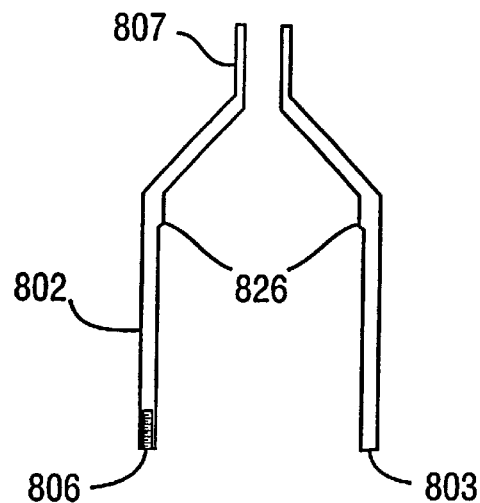
FIG. 8A is a cross-sectional view of a housing body for a housing assembly for an air flow assembly according to the present invention.
Figure 8B:
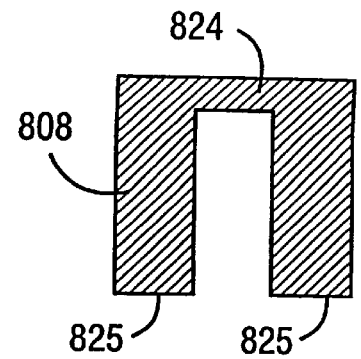
FIG. 8B is a cross-sectional view of a partition connector embodiment for a housing assembly for an air flow assembly according to the present invention.
Figure 8C:
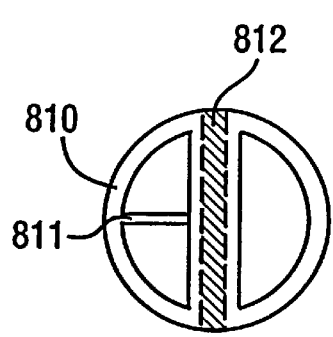
FIG. 8C is a bottom view of a flow control valve embodiment for a housing assembly for an air flow assembly according to the present invention.
Figure 8D:
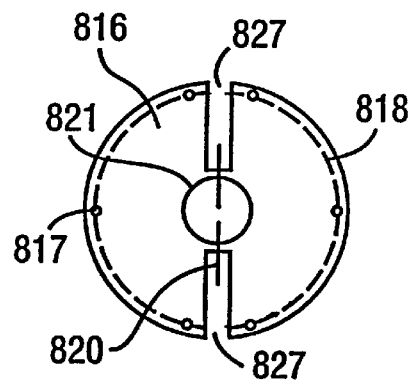
FIG. 8D is a top view of a sealing collar embodiment for a housing assembly for an air flow assembly according to the present invention.

The housing shown in FIGS. 8A–D contemplates inserting the air conduit into the housing and securing the vinyl film to two opposing partition connectors 808, as shown in FIG. 8B. To accomplish this, approximately 1½ inches of vinyl film may be left extending from the proximal end of the PVC tubing in the construction described above. This extra extension of vinyl film may then be sandwiched and glued with vinyl cement between the two opposing partition connectors 808. Partition connectors 808 may be flat pieces of acrylic shaped as shown in FIG. 8B. This completed partition connection assembly provides a support for flow control valve 810. In particular, flow control valve 810 may be attached to the top surface 824 of partition connectors 808. As shown in FIG. 8C, a notch 812 may be provided in flow control valve 810 to receive the top surface 824 of partition connectors 808. Flow control valve 810 may be made of a disk of Delrin (or similar material) with a diameter that corresponds to the inner diameter of the housing body 802, and with sections removed for the passage of air. Flow control valve 810 may also have a half-circle piece of rubber attached along the top face of flow control valve 810 opposite notch 812. The half-circle rubber piece then extends to the left side of the flow control valve 810 shown in FIG. 8C and rests on support member 811. The flow control valve and partition connection assembly are then inserted into the housing body 802. The flow control valve 810 rests against edges 826 shown in FIG. 8A. The sealing collar 816 may then be attached to bottom surface 803 of the housing body 802. Slot lines 827 in FIG. 8D receive the bottom legs 825 of partition connectors 808. The orientation of the flexible partition is shown by line 820 in FIG. 8D. Silicon gel sealant may again be applied to gaps and seams to provide a better seal of the entire construction.

Figure 9A:
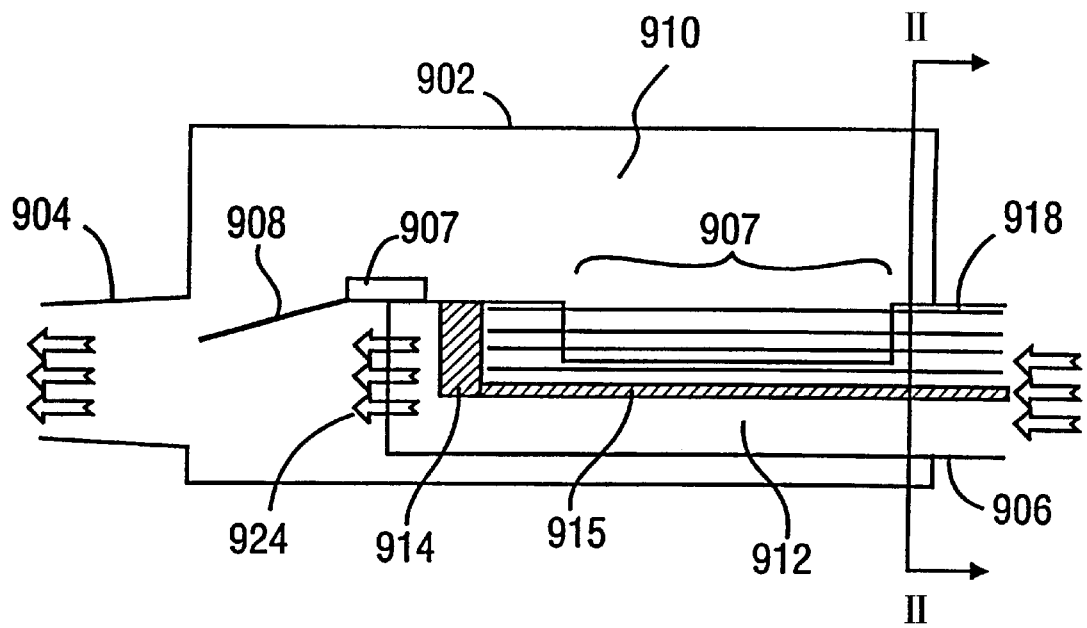
FIG. 9A is a cross-sectional side view of an oblate housing assembly for an air flow assembly according to the present invention during the exhalation process.
Figure 9B:
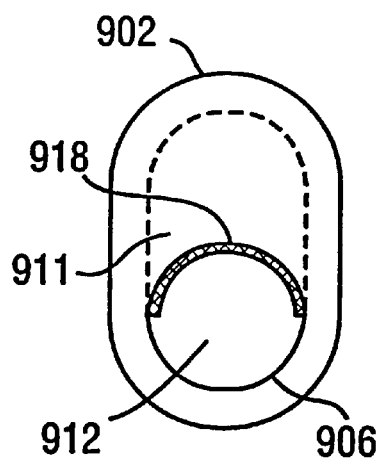
FIG. 9B is a cross-sectional end view along cut line II—II in FIG. 9A.
Figure 9C:
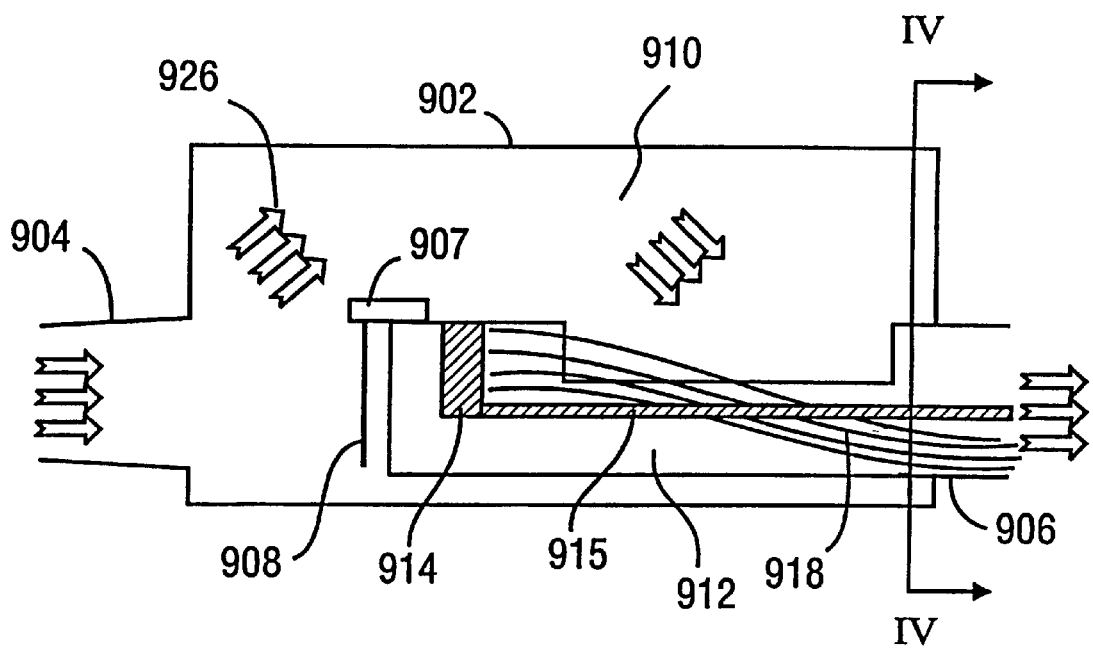
FIG. 9C is a cross-sectional side view of an oblate housing assembly for an air flow assembly according to the present invention during the exhalation process.
Figure 9D:
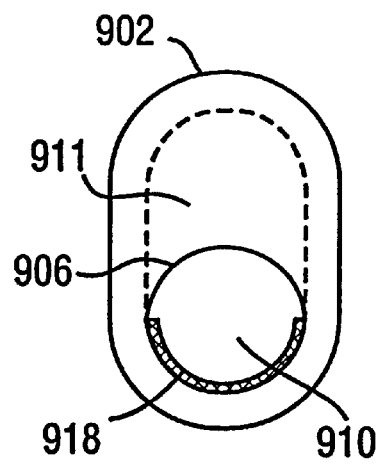
FIG. 9D is a cross-sectional end view along cut line IV—IV in FIG. 9C.

One concern in determining the structure to be used as the housing is to reduce air flow resistance. FIGS. 9A, 9B, 9C and 9D are an alternative embodiment of a housing or manifold according to the present invention that helps reduce air flow resistance to the exhalation gasses. FIGS. 9A and 9B shows the exhalation state of the housing, and FIGS. 9C and 9D shows the inhalation state of the housing. The housing may be oblate in shape and be made of a housing body 902 connected to a ventilator connection 904. Passageway 906 extends into the distal end of housing 902. An end piece is attached at area 911 at the distal end of housing body 902 to close the housing body 902, as shown in FIGS. 9B and 9D. The pieces that make up the housing may be made of acrylic tubing or acrylic sheets, which are cut or machined into the desired shapes. To reduce air flow resistance to the exhalation gasses 926, the cross section of passageway 906 may be made to match the cross section of the air conduit and of ventilator connection port 904, and passageway 906 may be aligned with the ventilator connection 904.

Passageway 906 may be formed using acrylic tubing. Flexible partition 918 is connected to the inside of passageway 906 along longitudinal line 915 and a partition attachment arc 914. The flexible partition 918 may be vinyl film as mentioned above. The acrylic tubing may also be cut in half along its longitudinal extension so that the vinyl film may be glued between the two halves, as discussed above with respect to the PVC tubing. In this manner, flexible partition 918 may be connected along the longitudinal line 915 of passageway 906 and along the upper wall of passage way 906 at the partition attachment arc 914. As discussed above, vinyl cement may be used to effectively glue the vinyl film in place. Passageway 906 may also have a window 907 cut into it to allow flow of inhalation gasses 926 into the air conduit that is attached to the distal end of passageway 906. A flow control valve 908 may be attached to passageway 906 using a valve attachment 907, which may be a square piece of acrylic attached to passageway 906. As mentioned above, silicon gel sealant may applied to gaps and seams to provide a better seal of the entire construction.

When assembled, the housing shown in FIGS. 9A–D provides a separate inhalation gas pathway 910 and a separate exhalation gas pathway 912. As shown in FIGS. 9C and 9D, inhalation gasses 926 flow through inhalation gas pathway 910 into the passageway forcing flexible partition 918 against the lower side of the passageway 906. As shown in FIGS. 9A and 9B, the exhalation gasses 924 flow through exhalation pathway 912. The flexible partition 918 is then forced against the upper side of passageway 906. In this manner, secretions within the intubated patient are forced out the exhalation gas pathway by each successive burst of exhalation gasses. To allow these secretions to exit the passageway 906, holes may be drilled or formed into the bottom of passageway 906. A recess or other secretion retaining area may then be provided within the housing for collecting and/or draining the pooled secretions.

Figure 10A:
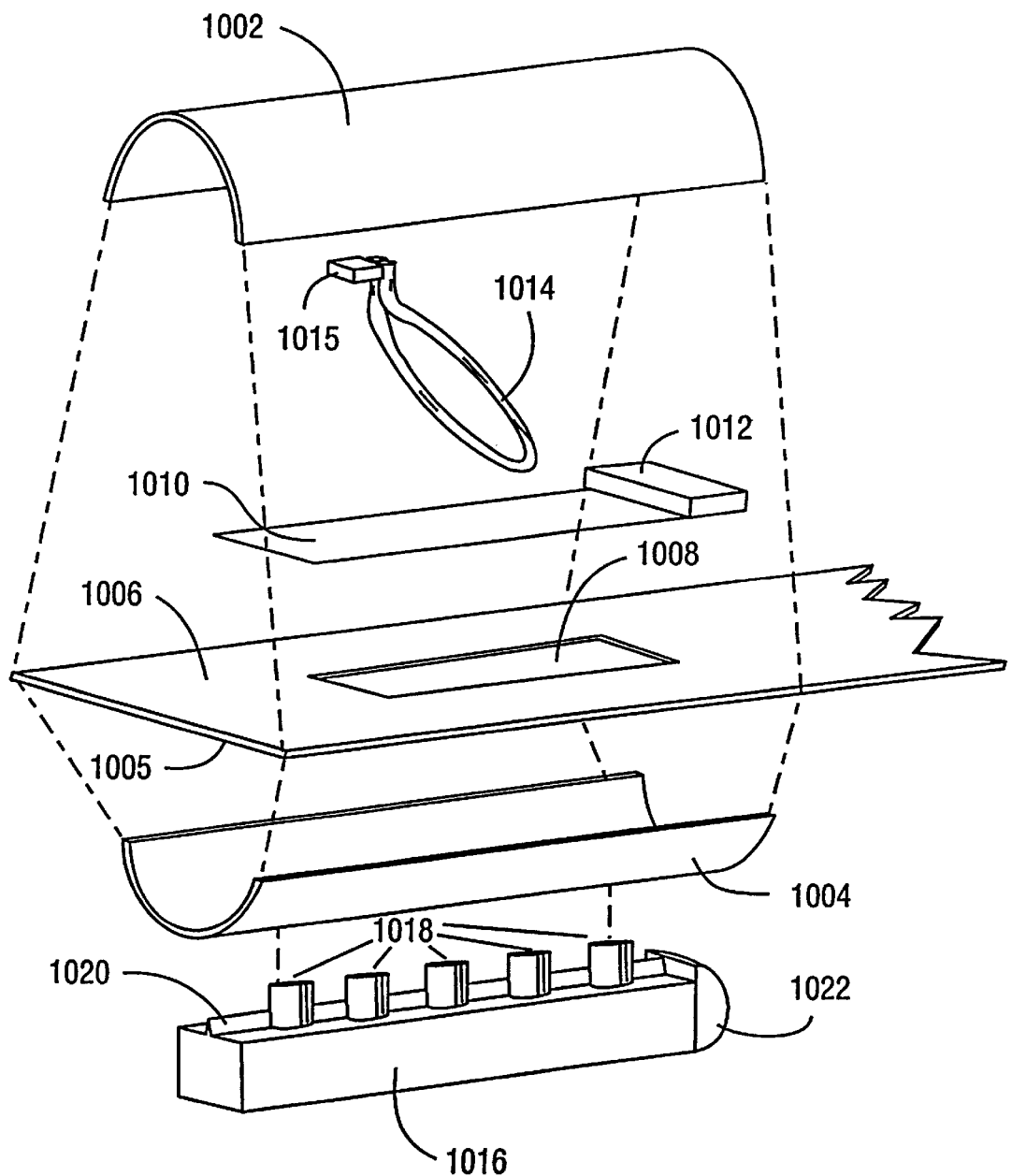
FIG. 10A is an exploded perspective view of a housing assembly for an air flow assembly according to the present invention.
Figure 10B:
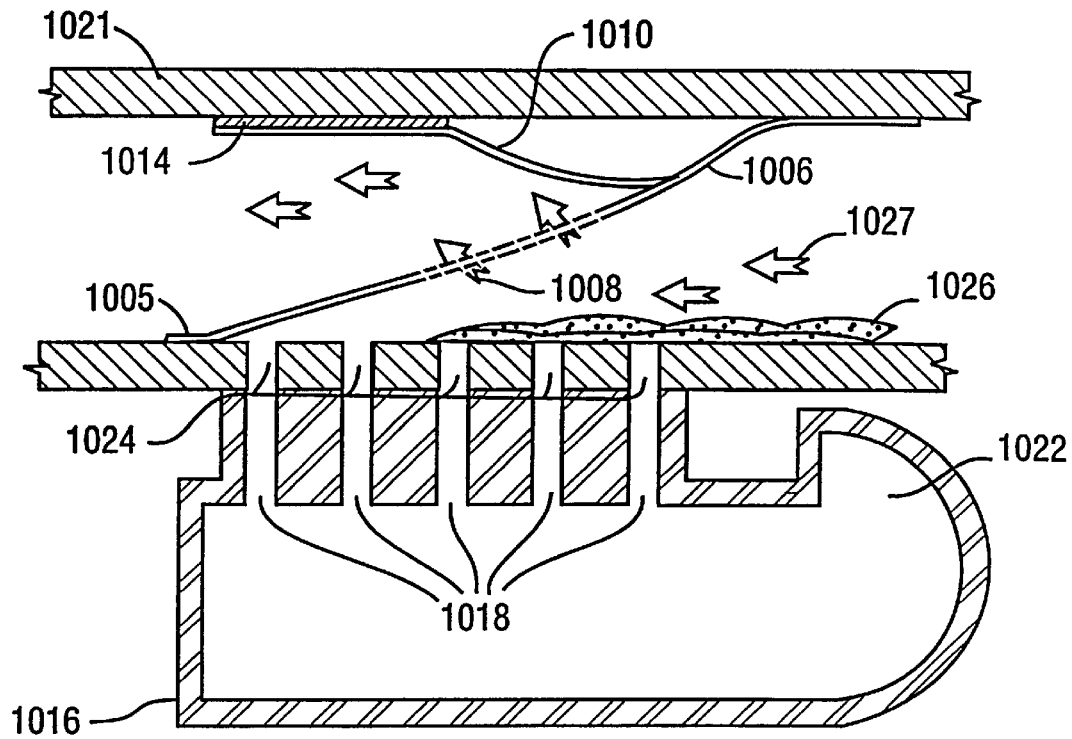
FIG. 10B is a cross-sectional side view of a housing assembly for an air flow assembly according to the present invention the during exhalation process.
Figure 10C:
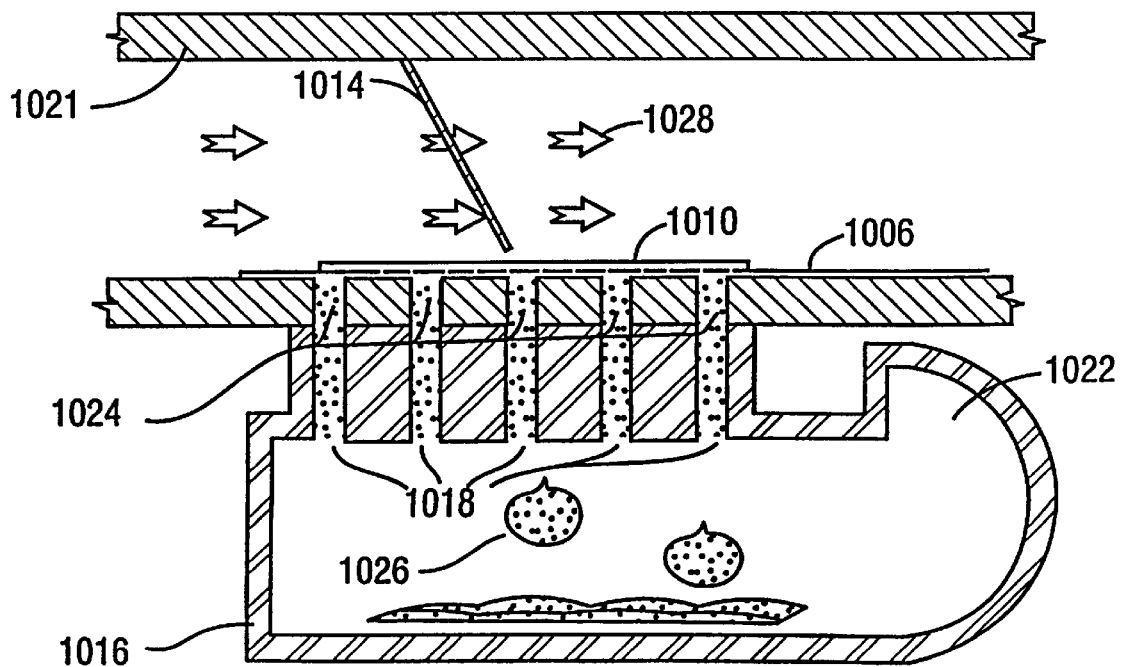
FIG. 10C is a cross-sectional side view of a housing assembly for an air flow assembly according to the present invention the during exhalation process.

FIGS. 10A, 10B, and 10C are a further embodiment of a housing or manifold according to the present invention that includes a reservoir positioned to hold secretions forced out of the patient's lungs. FIG. 10A shows a perspective view of this housing assembly. FIG. 10B shows a cross-sectional view of this housing assembly in its exhalation state. And, FIG. 10C shows a cross-sectional view of this housing assembly in its inhalation state. In FIGS. 10A–C, the patient would be positioned to the right of the drawing, and the outside air source would be positioned to the left of the drawing.

Looking to FIG. 10A, the housing assembly may include a tube 1021 that is made by joining together an upper tube half 1002 and lower tube half 1004. The tube 1021 may be slightly larger than the air conduit extending into the patient and may be connected to the air conduit. Tube 1021 may also be the end or proximal extension of the air conduit itself. As discussed above, partition 1006 may be held between the upper tube half 1002 and the lower tube half 1004 by applying vinyl cement along the longitudinal edges of the tube halves 1002 and 1004. The proximal edge 1005 of partition 1006 may be attached along the proximal inside surface of lower tube half 1004 to provide a sealed interface at the proximal end of partition 1006. A slot or port 1008 may be provided in partition 1006 to allow exhalation gasses to flow out from the patient as shown in FIG. 10B. Still looking to FIG. 10A, a flap 1010 may be attached at the distal end of the slot or port 1008. If desired, a hinge or attachment piece 1012 may be used to attach flap to partition 1006. Flap 1010 may also be attached at other places along the edges of port or slot 1008 such that flap 1010 acts to seal port or slot 1008 during inhalation as shown in FIG. 10C.

To urge flap 1010 to sealingly engage port or slot 1008, a proximal air flow control valve 1014 may be provided. Control valve 1014 may be a loop of nylon line or thin stainless steel wire as mentioned for the distal control valve discussed above. Control valve 1014 may be connected to valve connector 1015 that connects control valve 1014 to the inside surface of upper tube half 1002. Control valve 1014 extends downward toward the distal end of the housing and urges flap 1010 into sealing engagement over the slot or port 1008. This may be the natural or rest position for control valve 1014.

A reservoir 1016 may be provided to collect secretions pushed out of a patient's lungs through successive bursts of exhalation gasses. The reservoir 1016 may also include a semi-circular extension 1022 that will act as a secretion trap in supine patients. The reservoir 1016 shown in FIG. 10A is attached to the lower tube half 1004 and receives secretions from the tube through secretion inlets 1018. Secretion inlets 1018 may be supported by a support plate 1020 and may communicate with the tube through secretion outlets 1024 in the lower tube half 1004 (see FIGS. 10B and 10C). The secretion outlets 1024 may be formed by drilling holes into the bottom surface of lower tube half 1004.

During exhalation as shown in FIG. 10B, exhalation gasses 1027 force partition 1006 to the upper surface of the tube 1021 and flow from the patient through slot 1008 to the external air source, such as a ventilator. In flowing through slot 1008, exhalation gasses 1027 force flap 1010 and proximal flow control valve 1014 into an open position against the upper surface of the tube 1021. Secretions 1026 are pushed out of the patient by each successive burst of exhalation gasses and travel toward the proximal end 1005 of partition 1006. In so doing, secretions 1026 may enter secretion outlets 1024 and may then travel to the interior of reservoir 1016 to be collected.

During inhalation as shown in FIG. 10C, inhalation gasses 1028 force partition 1006 to the lower portion of the tube and flow from the air source to the patient. Proximal flow control valve 1014 extends downward and urges flap 1010 closed against partition 1006. In this process, secretions 1026 tend to be pushed down through secretion outlets 1024 and reservoir inlets 1018 to be collected within the reservoir 1018.

Figure 11:
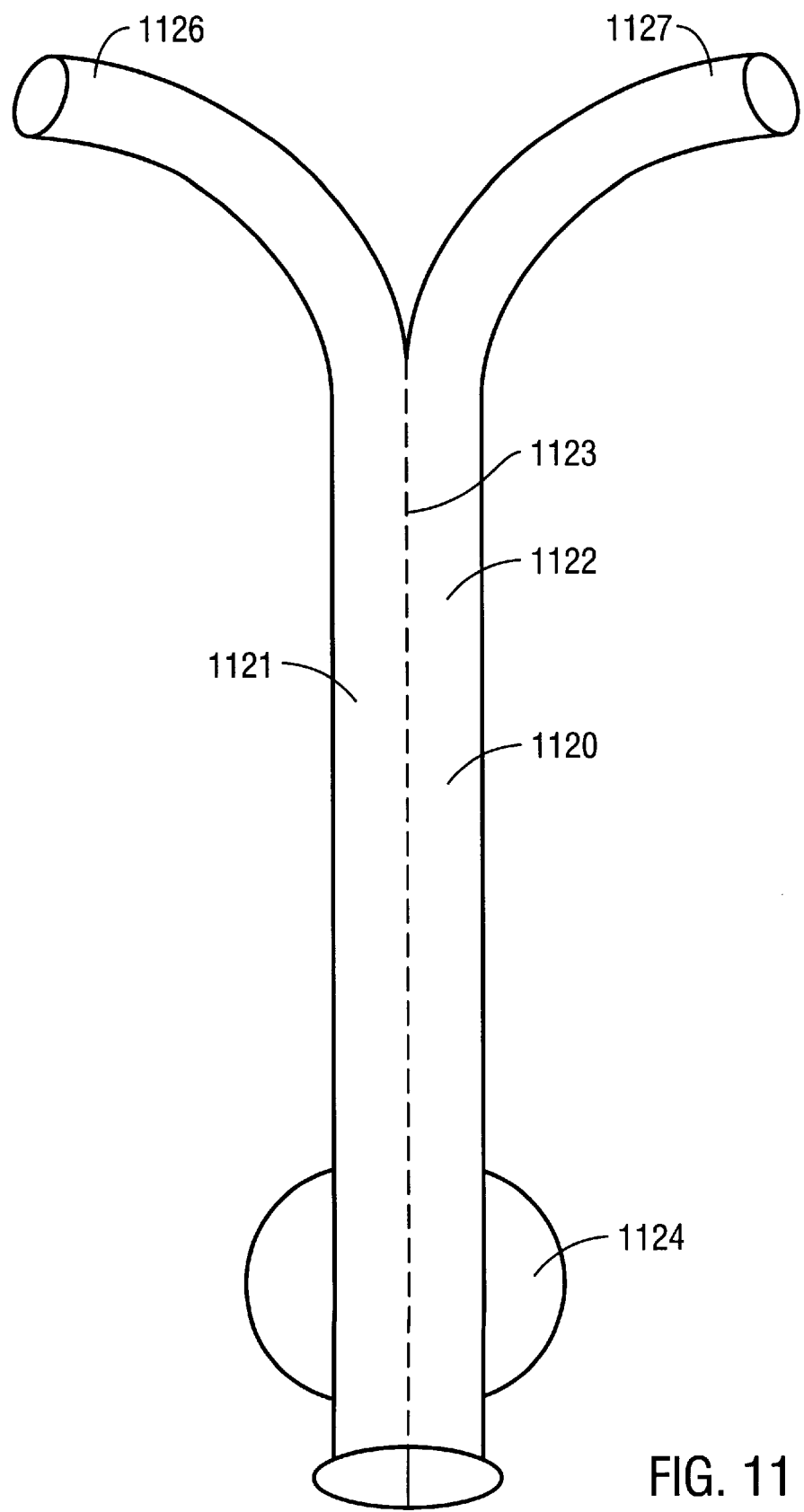
FIG. 11 is a cross-sectional side view of an alternative embodiment of an air flow assembly according to the present invention.

FIG. 11 is a schematic drawing of an alternative embodiment of an endotracheal tube flow assembly according to the present invention. Endotracheal tube 1120 is shown in cross sectional view. A separate inspiratory pathway 1121 and expiratory pathway 1122 are formed by partition 1123 within endotracheal tube 1120. Inspiratory pathway 1121 is contiguous with inspiratory inlet tube 1126. Likewise, expiratory pathway 1122 is contiguous with expiratory outlet tube 1127. Because each of the inspiratory pathway 1121 and expiratory pathway 1122 are separate from each other, yet share a common endotracheal tube, this embodiment of the present invention is particularly applicable to a variety of ventilation applications, including partial liquid ventilation of patients.

Endotracheal tube 1120 has an inflatable cuff 1124. Inflatable cuff 1124 may be inflated to seal trachea (not shown) except for air flow through endotracheal tube 1120. As contemplated by the present invention, endotracheal tube 1120 may also take the form of other air conduits inserted into a patient's trachea or lungs, such as a tracheostomy tube. An endotracheal tube embodiment is described because they are commonly used in intubating a patient.

Comparing the intratracheal tube of the present invention compared to a standard tracheostomy tube showed that the preset tube provided superior secretion removal while avoiding routine tracheal suctioning. Moreover, quantitative cultures indicated a greatly reduced level of microbial contamination. To evaluate these parameters, a tracheostomy was performed on 6 anesthetized sheep for the placement of a standard 7.5 Shiley tracheostomy tube in three animals, and the intratracheal tube of the present invention was placed in the other three animals. Pulmonary injury was induced using a modified bee smoker. The animals were awake and mechanically ventilated in metabolic cages. The tracheostomy tubes ere suctioned every 4 hours, and the intratracheal tubes of the present invention were not suctioned unless obstruction occurred. Hemodynamics, airway pressures, volume of secretions suctioned, and volume of secretions collected in expiratory traps were measured every 4 hours for 48 hours. quantitative cultures ere obtained from the hub of the tracheostomy tubes, the inspiratory and expiratory hubs of the intratracheal tubes of the present invention, and from biopsies of both lungs of each animal post-mortem.

The results indicated that no significant difference was found in airway pressures or hemodynamics between the two types of tubes. The intratracheal tube of the present invention, however, cleared significantly more secretions ($60.3 \pm 5.2$ ml) than the control Shiley tracheostomy tube ($46.4 \pm 3.5$ ml) every 4 hours for 48 hours, $p<0.05$. Moreover, the results indicate that in both sheep lungs, the animals intubated with the Shiley tracheostomy tube had more microbial growth than in lungs intubated with the tube of the present invention. The same pattern was also shown for microbial growth from the intratracheal tubes; the inspiratory side of the present invention showed less contamination than the expiratory side of the present invention, and both sides showed less contamination than the Shiley tracheostomy tube.

In the embodiments discussed with respect to FIGS. 8A–D, FIGS. 9A–D, FIGS. 10A–C, and FIG. 11, the following materials may be utilized:

air conduit PVC tubing from endotracheal or tracheostomy tube flexible partition vinyl film (0.002" thick)

housing/passageway acrylic tubing and/or acrylic sheet (1/16" thick)

distal flow control valve thin stainless steel wire or nylon fishing line proximal flow control valve Delrin sheet (1/4" thick)

control valve flap thin rubber sheet screws for sealing collar socket head screws (0–80, 3/16" long)

vinyl cement IPS weld-on 1784 vinyl cement (IPS Corp., Gardenal, Calif.

silicon sealant GE Silicone II Household Glue & Seal (GE Silicones, Waterford, N.Y.)

miscellaneous sealant Goop Household Adhesive & Sealant (Eclectic Products, Inc., Carson, Calif.)

It should be noted that these materials are meant only to be an example and may be modified without parting from the present invention.

EXAMPLE 2

Partial Liquid Ventilation (PLV)

Liquid ventilation of patients has been utilized where the patient is at high risk or mortality due to acute respiratory failure. Gas exchange is observed to improve in most patients, and is frequently accompanied by an improvement in tidal volume and compliance.

The trachea is reintubated with a perfluorocarbon-compatible endotracheal tube of the present invention, and baseline bronchoscopy and chest radiography are performed. Time-cycled, pressure-controlled ventilation is used to generate a peak inspiratory pressure that produced the following evidence of early overdistention on the dynamic pressure volume curve (usually about 30 to about 40 cm $H_2O$); positive end-expiratory pressure (PEEP), about 6 cm $H_2O$; respiratory rate, about 20 breaths per min; inspiratory expiratory ratio of about 1:1; and fraction of inspired oxygen ($FIO_2$), about 1.0.

Baseline data may be collected during a 15-min period of discontinuation of ECLS or while the extra-corporeal blood flow is maintained at minimal ECLS flow in those patients who could not tolerate ECLS flow discontinuation. In such patients, the extracorporeal blood flow rate is reduced to a level that maintained the arterial oxygen saturation ($SaO_2$) at approximately 90% (minimal ECLS flow). Perflubron (C8F17Br1, LiquiVent; Alliance Pharmaceutical Corp, San Diego, Calif.) is a radiopaque, inert, colorless fluid that carries a large quantity of oxygen (50 mL of oxygen per deciliter of perflubron) and $CO_2$ (210 mL of $CO_2$ per deciliter of perflubron), and has the consistency of water, a high specific gravity (density, 1.93 g/mL), low viscosity (1.10 centistokes), and low surface tension (18 dyne/cm). Perflubron is an perfluorocarbon fluid with eight carbon chain in which all potential sites are bonded to a fluorine atom, except for a terminal bromine. On this particular perfluorocarbon, this confers a radiopaque character that is an advantage when assessing the degree of lung filling and he distribution of the perflubron. As herein used, an oxygen exchange fluid includes liquids having a high ability to carry a large quantity of oxygen and $CO_2$. An example of a representative oxygen exchange fluid is Perflubron, although it is recognized that many oxygen exchange fluids with similar characteristics may be used in the present invention.

Perflubron at doses of about 2.5 to about 10 mL/kg of body weight may be administered via the endotracheal tube over a 5- to 15-min period. Dosing of perflubron is repeated at approximately 30-min intervals until a sustained meniscus is noted to be present at the level of the sternum within the endotracheal tube. The initial dose of perflubron administered is a median of about 19 mL/kg (range, about 7 to about 40 mL/kg). During PLV, the lungs may be ventilated at settings as described.

With each respiratory cycle, it appears that oxygen gas distributes via the airways into alveoli as alveolar gas/perfluorocarbon oxygen tensions are increased. Simultaneously, $CO_2$ is eliminated as alveolar gas/perfluorocarbon $CO_2$ levels decrease. Data collection at minimal ECLS flow and during transient discontinuation of ECLS is then performed along with repeat bronchoscopy and anteroposterior and lateral chest radiography. Because of moderate volatility, some of the perflubron may evaporate over the ensuing 24 h. To maintain the lungs filled, addition of perflubron is performed on a daily basis with a mean cumulative perflubron dose of about 38 mL/kg (range, about 15 to about 65 mL/kg) administered into the trachea over a 1- to 7-day period. The decision to redose is based on the following: (1) amount of remaining radiopaque perflubron visualized on the lateral chest radiograph; (2) presence of a perflubron meniscus on examination of the endotracheal tube during transient ventilator disconnection; and (3) sustained lung recovery such that discontinuation of ECLS is anticipated.

Efficiency of the procedure is measured by determining the physiologic shunt and pulmonary compliance. Radial artery and pulmonary artery blood $PO_2$, $PCO_2$, pH, hemoglobin, an oxygen saturation are assessed at baseline, after each dose of Perflubron, and daily during the course of treatment, utilizing a blood gas analyzer and an oximeter. Physiologic shunt is determined based on the following equation: $Qps/Qt=([CiO_2—CaO_2]/[CiO_2—CvO_2])$, where Qps is the physiologic shunt, Qt is the cardiac output, $CaO_2$ is the oxygen content of the arterial blood, measured in mL/dL, $CvO_2$ is the oxygen content of mixed venous blood, and $CiO_2$ blood that is fully equilibrated with alveolar partial pressure of oxygen ($P_AO_2$, measured in mL/dL). The equation assumes that under optimal circumstances, pulmonary capillary blood completely equilibrates with $P_AO_2$. Therefore, with an $FIO_2$ of 1.0, the pulmonary venous partial pressure of oxygen ($PvO_2$) and $PAO^2$ will both be about 690 mm Hg. Blood that leaves the lungs without being fully equilibrated with alveolar oxygen will contribute to a deviation from the optimal pulmonary $PAO_2$ and, therefore, the optimal $PvO_2$ content. The greater the fraction of pulmonary blood flow that is incompletely oxygenated, the larger the deviation from the optimal and the greater the "shunt."

Pressure controlled ventilation maybe controlled by computer. Expired gas tidal volumes may be corrected for ventilator tubing compliance. Static pulmonary compliance is calculated as the measured tidal volume divided by the difference between the peak inspiratory plateau pressure and the PEEP in cm $H_2O$. The static pulmonary compliance may be corrected for the weight of each individual patient.

Additional physiologic data, may include systemic arterial blood pressure, pulmonary artery blood pressure, pulmonary capillary wedge pressure, temperature, heart rate, and ventilator settings. Cardiac output may be evaluated by the hemodilution technique, using ventricular saline injections and a cardiac output monitor. Pulmonary vascular resistance index (PVRI) is calculated by the formula: PVRI= ([MPAP−PCWP]/CI) where MPAP indicates mean pulmonary artery pressure (mm Hg); PCWP is the pulmonary capillary wedge pressure (mm Hg), and CI is the cardiac index (L-min$^{-1}$m$^{-2}$).

The present invention also finds use in improving the administration of perflubron or other gas exchange medium to the lungs, Pulmonary blood flow, which is mainly distributed to the atelectatic and consolidated dependent lung regions, may be redistributed to non-dependent zones because of he weight of the perfluorocarbon within the lungs. In addition, the present invention is useful in removing exudate from the peripheral airways and alveoli without the need for suctioning, which requires the periodic efforts of a trained health care professional and often occurs on an intermittent basis. In some patients, mucus plug formation may occur more frequently during partial liquid ventilation than under normal ventilation. Thus, the present invention will find great use in such procedures.

Further modifications and alternative embodiments of this invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as the presently preferred embodiments. Various changes may be made in the shape, size, and arrangement of parts. For example, equivalent elements or materials may be substituted for those illustrated and described herein, and certain features of the invention may be utilized independently of the use of other features, all as would be apparent to one skilled in the art after having the benefit of this description of the invention.

What is claimed is:

1. An air flow assembly for directing air flow within a patient to facilitate partial liquid ventilation and removal of secretions from within the patient without aspiration, said assembly comprising:

an air conduit positionable within a patient and configured to deliver an oxygen exchange fluid, the air conduit having an inspiratory pathway and an expiratory pathway formed within said air conduit;

a conduit coupling assembly including a housing having an upper and a lower port; and air flow control means disposed within said housing for directing inhalation gasses through said inspiratory pathway and for allowing exhalation gasses to pass through said expiratory pathway to force secretions out of said patient through said expiratory pathway without aspiration.

2. The air flow assembly of claim 1, further comprising an inspiratory inlet tube coupled to said inspiratory pathway and an expiratory outlet tube coupled to the expiratory pathway.

3. The air flow assembly of claim 2, wherein the inspiratory inlet tube is integrally formed with the inspiratory pathway and the expiratory outlet tube is integrally formed with the expiratory pathway.

4. The air flow assembly of claim 1, wherein the inspiratory pathway and the expiratory pathway are formed by a longitudinal partition positioned to divide the air conduit into separate portions.

5. The air flow assembly of claim 4, wherein the partition divides the air conduit into substantially equal separate portions, forming the inspiratory pathway and the expiratory pathway.

6. The air flow assembly of claim 4, wherein the partition is a flexible partition.

7. The air flow assembly of claim 4, wherein the partition is a rigid partition.

8. The air flow assembly of claim 1, wherein said air conduit is tracheostomy tube.

9. The air flow assembly of claim 1, wherein the inspiratory pathway and the expiratory pathway are formed by separate tubes within the air conduit.

10. A method for performing partial liquid ventilation of a patient and for removing secretions from lungs of the patient, comprising:

intubating a patient with an air conduit having an inspiratory pathway and a separate expiratory pathway;

filling at least a portion of the patient's lungs with an oxygen exchange fluid;

directing a gas down said inspiratory pathway under flow conditions sufficient to allow gas exchange with the oxygen exchange fluid;

allowing exchanged gas to exit the patient's lungs through said expiratory pathway and to move secretions within the lungs up the expiratory pathway; and separating the secretions from the exchanged gas at a proximal end of the expiratory pathway.

11. The method of claim 10, wherein said intubating step comprises:

inserting an air conduit within said patient; and inserting an insertable flow control assembly within said air conduit to define with said air conduit said inspiratory pathway and said separate expiratory pathway.

12. The method of claim 10, wherein the oxygen exchange fluid is a perfluorocarbon fluid.

13. The method of claim 10, wherein said air conduit is tracheostomy tube.

14. A method for performing partial liquid ventilation of a patient and for removing secretions from lungs of the patient, comprising:

intubating a patient with an air flow assembly having a separate inspiratory pathway and a separate expiratory pathway, the air flow assembly comprising an air conduit positionable within a patient, the air conduit having the inspiratory pathway and the expiratory pathway formed within the air conduit by a longitudinal partition positioned to divide the air conduit into separate portions with an inspiratory inlet tube coupled to said inspiratory pathway and an expiratory outlet tube coupled to the expiratory pathway;

filling at least a portion of the patient's lungs with an oxygen exchange fluid;

directing a gas down said inspiratory pathway under flow conditions sufficient to allow gas exchange with the oxygen exchange fluid;

allowing exchanged gas to exit the patient's lungs through said expiratory pathway and to move secretions within the lungs up the expiratory pathway; and separating the secretions from the exchanged gas at a proximal end of the expiratory pathway.

15. The method of claim 14, wherein the oxygen exchange fluid is a perfluorocarbon fluid.

* * * * *